US006808876B1

(12) United States Patent
Kruger et al.

(10) Patent No.: US 6,808,876 B1
(45) Date of Patent: Oct. 26, 2004

(54) CELLULAR REGULATORS OF INFECTIOUS AGENTS AND METHODS OF USE

(75) Inventors: Martin Kruger, Hannover (DE); Peter J. Welch, San Diego, CA (US); Jack R. Barber, San Diego, CA (US)

(73) Assignee: Immusol, Inc., San Diego, CA (US)

( * ) Notice: Subject to any disclaimer, the term of this patent is extended or adjusted under 35 U.S.C. 154(b) by 0 days.

(21) Appl. No.: 09/563,794

(22) Filed: May 2, 2000

(51) Int. Cl.[7] .......................... C12N 15/00; C12Q 1/68; C07H 21/02
(52) U.S. Cl. ......................... 435/5; 435/6; 435/320.1; 435/69.1; 435/69.7; 435/DIG. 1; 435/DIG. 3; 435/DIG. 34; 435/DIG. 37; 536/23.1; 536/24.5
(58) Field of Search ....................... 435/5, 6, 69.1, 435/69.7, 320.1, DIG. 1, DIG. 3, DIG. 34, DIG. 37; 536/23.1, 24.5

(56) References Cited

U.S. PATENT DOCUMENTS

| 4,861,719 A | 8/1989 | Miller ........................ 435/236 |
| 5,124,263 A | 6/1992 | Temin et al. ............. 435/240.2 |
| 5,219,740 A | 6/1993 | Miller et al. ................ 435/69.6 |
| 5,254,678 A | 10/1993 | Haseloff et al. ........... 536/23.2 |
| 5,354,855 A | 10/1994 | Cech et al. ................. 536/24.1 |
| 5,496,698 A | 3/1996 | Draper et al. ................... 435/6 |
| 5,574,143 A | 11/1996 | Haseloff et al. ........... 536/23.2 |
| 5,580,967 A | 12/1996 | Joyce ......................... 536/23.2 |
| 5,610,054 A | 3/1997 | Draper ....................... 435/363 |
| 5,616,459 A | 4/1997 | Kramer et al. .................. 435/5 |
| 5,759,773 A | 6/1998 | Tyagi et al. .................... 435/6 |

FOREIGN PATENT DOCUMENTS

| EP | 1074617 | 2/2001 |
| WO | WO 92/01806 | 2/1992 |
| WO | WO 93/23569 | 11/1993 |
| WO | WO 94/26877 | 11/1994 |
| WO | WO 96/01314 | 1/1996 |
| WO | WO/98 32880 | 7/1998 |
| WO | WO 98/32880 | 7/1998 |
| WO | WO/00 05415 | 2/2000 |
| WO | WO 00/05415 | 2/2000 |
| WO | WO/00 11171 | 3/2000 |
| WO | WO/00 58473 | 10/2000 |
| WO | WO/01 55301 | 8/2001 |

OTHER PUBLICATIONS

Welch et al., Gene Therapy, 1996, vol. 3, pp. 994–100.*
Price et al., Biochem. J., 1996, vol. 318, pp. 631–636.*
GenBank accession number AA703831 Dec. 1997.
GenBank accession number AI800599.1 Jul. 6, 1999.
GenBank accession number AI632282.1 Apr. 1999.
GenBank accession number W58368 May 1996.
GenBank accession number W58049 May 1996.
GenBank accession number AI660531.1 May 1999.
GenBank accession number AI798535.1 Jul. 1999.
GenBank accession number AI143649 Sep. 1998.
GenBank accession number AI040925 Aug. 1998.
GenBank accession number AA102365 Jun. 1996.
GenBank accession number AA991764 Jun. 1998.
GenBank accession number AA587233 Sep. 1997.
GenBank accession number AA580025 Sep. 1997.
GenBank accession number AI637675.1 Apr. 1999.
GenBank accession number W22190 May 1996.
GenBank accession number AI937500.1 Aug. 1999.
GenBank accession number T78051 Mar. 1995.
GenBank accession number R38705 May 1995.
GenBank accession number T90276 Mar. 1995.
GenBank accession number T82858 Mar. 1995.
GenBank accession number AA507077 Jul. 1997.
GenBank accession number Z41323 Nov. 1994.
GenBank accession number Z45650 Nov. 1994.
GenBank accession number AA649500 Jul. 1997.
GenBank accession number T5394 Mar. 1995.
GenBank accession number AI700227.1 Jun. 1999.
GenBank accession number F01614 Feb. 1995.
GenBank accession number AI359536 Jan. 1999.
GenBank accession number AA582198 Sep. 1997.
GenBank accession number F00408 Mar. 1995.
GenBank accession number AA322492 Apr. 1997.
GenBank accession number Z24924 Aug. 1993.
GenBank accession number F31617.1 May 1999.
GenBank accession number AA102364 Jun. 1996.
GenBank accession number AA905387 Mar. 1998.
GenBank accession number C21034 Oct. 1996.
GenBank accession number F05355 Feb. 1995.
GenBank accession number AA933569 May 1998.
GenBank accession number F34596.1 May 1999.
GenBank accession number AI970443.1 Aug. 1999.
GenBank accession number AA308943 Apr. 1997.
GenBank accession number AA323715 Apr. 1997.
GenBank accession number R61886 May 1995.
GenBank accession number AA130818 Oct. 1997.
GenBank accession number AA311999 Apr. 1997.
GenBank accession number AA076401 Oct. 1997.
GenBank accession number U38253 Oct. 1995.
GenBank accession number L19161.
Akhtar et al., "Molecular DIY with hairpins and hammerheads," *Nature Medicine* 1:300–302 (1995).

(List continued on next page.)

*Primary Examiner*—Padmashri Ponnaluri
(74) *Attorney, Agent, or Firm*—Foley & Lardner LLP

(57) ABSTRACT

A method of identifying a compound that modulates the activity of a cellular regulator is provided. The method consists of contacting a sample containing a cellular regulator and a nucleic acid element acted on by the cellular regulator with a test compound under conditions that allow replication or expression of the nucleic acid element or a gene or mRNA operatively linked to the nucleic acid element or gene, and an increase or decrease in the amount of replication or expression in the presence of the test compound compared to the absence of the test compound indicates that the compound has cellular regulator modulatory activity. A method of treating a HCV infection is also provided.

5 Claims, 13 Drawing Sheets

OTHER PUBLICATIONS

Albuquerque–Silva et al., "Ribozyme–mediated decrease in mumps virus nucleocapsid mRNA level and progeny in infected vero cells," *Antisense & Nucleic Acid Drug Development* 9:279–288 (1999).

Ali and Siddiqui, "The La antigen binds 5' noncoding region of the hepatitis C virus RNA in the context of the initiator AOG codon and stimulates internal ribosome entry site–mediated translation," *Proc. Natl. Acad. Sci. U.S.A.* 94:2249–2254 (1997).

Anderson et al., "Mutagenesis of the hairpin ribozyme," *Nucleic Acids Res.* 22:1096–1100 (1994).

Ausubel et al., *Current Protocols in Mol. Biol.*, (Supplement 50) John Wiley and Sons, Baltimore, MD (2000).

Bennett and Cullimore, "Selective cleavage of closely–related mRNAs by synthetic ribozymes," *Nucleic Acids Research* 20:831–837 (1992).

Berzal–Herranz et al., "In vitro selection of active haripin ribozymes by sequential RNA–catalyzed cleavage and ligation reactions," *Genes and Development* 6:129–134 (1992).

Buratti et al., "Functional analysis of the interaction between HCV 5'UTR and putative subunits of eukaryotic translation initiation factor eIF3," *Nucleic Acids Res.* 26:3179–3187 (1998).

Cameron and Jennings, "Specific gene suppression by engineered ribozymes in monkey cells," *Proc. Natl. Acad. Sci. U.S.A.* 86:9139–9143 (1989).

Campbell and Cech, "Indentification of ribozymes within a ribozyme library that efficiently cleave a long substrate RNA," *RNA* 1:598–609 (1995).

Cech and Bass, "Biological catalysis by RNA," *Ann. Rev. Biochem* 55:599–629 (1986).

Cech and Uhlenbeck, "Hammerhead nailed down," *Nature* 372:39–40 (1994).

Cheng et al., "Unique spectrum of activity of 9–[(1,3–dihydroxy–2–propoxy) methyl]–guanidine against herpes viruses in vitro and its mode of action against herpes simplex virus type 1," *Proc. Natl. Acad. Sci. U.S.A.* 80:2767–1770 (1983).

Chowrira et al., "Ionic requirements for RNA binding, cleavage, and ligation by the hairpin ribozyme," *Biochemistry* 32:1088–1095 (1993).

De Young et al., "Catalytic properties of hairpin ribozymes derived from chicory yellow mottle virus and arabis mosaic virus satellite RNAs," *Biochemistry* 34:15785–15791 (1995).

Dropulić et al., "Functional characterization of a U5 ribozyme: intracellular suppression of human immunodeficiency virus type 1 expression," *J. Virol.* 66:1432–1441 (1992).

Gold et al., "Diversity of oligonucleotide functions," *Annu. Rev. Biochem.*, 64:763–797 (1995).

Gold et al., "From oligonucleotide shapes to genomic SELEX: Novel biological requlatory loops," *Proc. Natl. Acad. Sci. USA*, 94:59–64 (1997).

Gold et al., "SELEX and the evolution of genomes," *Current Opinion in Genetics & Development*, 7:848–851 (1997).

Hellen et al., "A cytoplasmic 57–kDa protein that is required for translation of picornavirus RNA by internal ribosomal entry is identical to the nuclear pyrimidine tract–biding protein," *Proc. Natl. Acad. Sci. U.S.A.* 90:7642–7646 (1993).

Ho et al., "Potent antisense oligonucleotides to the human multidrug resitance–1 mR are rationally selected by mapping RNA–accessible sites with oligonucleotide libraries," *Nucleic Acids Res.* 24:1901–1917 (1996).

Jackson and Kaminski, "Internal initiation of translation in eukaryotes: the picornavirus paradigm and beyond," *RNA* 1:985–1000 (1995).

Kijima et al., "Therapeutic applications of ribozymes," *Pharmac. Ther.* 68:247–267 (1995).

Lavrovsky et al., "Ribozyme–mediated cleavage of the estrogen receptor messenger RNA and inhibition of receptor function in target cells," *Mol. Endocrinol.* 13:925–934 (1999).

Lazarev et al., "Inhibition of influenza A virus reproduction by a ribozyme targeted against PB1 mRNA," *Antiviral Res.* 42:47–57 (1999).

Lewin et al., "Ribozyme rescue of photoreceptor cells in a transgenic rat model of autosomal dominant retinitis pigmentosa," *Nat. Med.* 4:967–971 (1998).

Lieber and Strauss, "Selection of efficient cleavage sites in target RNAs by using a ribozyme expression library," *Molecular and Cellular Biology*, 15:540–551 (1995).

Lu and Wimmer, "Poliovirus chimeras replicating under the translational control of genetic elements of hepatitis C virus reveal unusual properties of the internal ribosomal entry site of hepatitis, C virus," *Proc. Natl. Acad. Sci. U.S.A.* 93:1412–1417 (1996).

Macjak and Draper, "Design of quasi–random ribozyme expression vectors," *J. Cell. Biochem.* Supplement 17E, S206:202 (1993).

Macejak et al., "Adenovirus–mediated expression of a ribozyme to c–myb mRNA inhibits smooth muscle cell proliferation and neointima formation in vivo," *J. Virol.* 73:7745–7751 (1999).

Miller and Miller, "Phosphorylation of acyclovir (acycloguanosine) monophosphate by GMP kinase," *J. Biol. Chem.* 255:7204–7207 (1980).

Ohkawa et al., "Cleavage of viral RNA and inhibition of viral translation by heaptitis C virus RNA–specific hammerhead ribozyme in vitro," *J. Hepatol.* 27:78–84 (1997).

Ojwang et al., "Inhibition of human immunodeficiency virus type 1 expression by a hairpin ribozyme," *Proc. Natl. Acad. U.S.A.* 89:10802–10806 (1992).

Ozaki et al., "Ribozyme–mediated specific gene replacement of the alpah1–antitrypsin gene in human hepatoma cells," *J. Hepatol.* 31:53–60 (1999).

Pestova et al., "Canonical eukaryotic initiation factors determine initiation of translation by internal ribosomal entry," *Mol. Cell. Biol.* 16:6859–6869 (1996).

Pestova et al., "A prokaryotic–like mode of cytoplasmic eukaryotic ribosome binding to the initiation codon during internal translation initiation of hepatitis C and classical swine fever virus RNAs," *Genes Dev.* 12:67–83 (1998).

Price and Proud, "The guanine nucleotide–exchange factor," eIF–2B, *Biochimie.* 76:748–760 (1994).

Price et al., "Cloning of cDNA for the gamma–subunit of mammalian translation initiation factor 2B, the guanine nucleotide–exchange factor for eukaryotic initiation factor 2," *Biochem J.* 318:631–636 (1996).

Reynolds et al., "Unique features of internal initiation of hepatitis C virus RNA translation," *EMBO J.* 14:6010–6020 (1995).

Sakamoto et al., "Intracellular cleavage of hepatitis C virus RNA and inhibition of viral protein translation by hammerhead ribozymes," *J. Clin. Invest.* 98:2720–2728 (1996).

Sambrook, et al., Molecular Cloning, A Laboratory Manual, Cold Spring Harbor Laboratory Press, NY Second Edition, 1989.

Sioud et al., "Preformed ribozyme destroys tumour necrosis factor mRNA in human cells," *J. Mol. Biol.* 223:831–835 (1992).

Sizova et al., "Specific interation of eukaryotic translation initiation factor 3 with the 5' nontranslated regions of hepatitis C virus and classical swine fever virus RNAs," *J. Virol.* 72:4775–4782 (1998).

Thompson et al., "Ribozymes in gene therapy," *Nature Medicine* 1:277–278 (1995).

Welch et al., "A potential therapeutic application of hairpin ribozymes: In vitro and in vivo studies of gene therapy for hepatitis C virus infection," *Gene Therapy* 3:994–1001 (1996).

Welch et al., "Intracellular application of hairpin ribozyme genes against hepatitis B virus," *Gene Therapy* 4:736–743 (1997).

Yu et al., "A hairpin ribozyme inhibits expression of diverse strains of human immunodeficiency virus type 1," *Proc. Natl. Acad. Sci. USA* 90:6340–6344 (1993).

Yu et al., "Intracellular immunization of human fetal cord blood stem/progenitor cells with a ribozyme against human immunodeficiency virus type 1," *Proc. Natl. Acad. Sci. USA* 92:699–703 (1995).

Yu et al., "In Vitro and in Vivo characterization of a second functional hairpin ribozyme against HIV–1," *Virology* 206:381–386 (1995).

Zhang et al., "Antisense oligonucleotide inhibition of hepatitis C virus (HCV) gene expression in livers of mice infected with an HCV–vaccinia virus recombinant," *Antimicrob. Agents Chemother.* 43:347–354 (1999).

Krueger, et al., "Identification of eIF2gamma and eIF2gamma as cofactors of hepatis C virus internal ribosome entry site–mediated translation using a functional genomics approach," *Proceedings of the National Academy of Sciences of the United States,* 97(155):8566–8571 (2000).

* cited by examiner

A. Control Rz (RzBR1)

C. RzUCUU

B. RzUCGA

D. RzGACG

| RIBOZYME | SEQUENCE Helix 1 | | Helix 2 | TARGET GENE (MATCH) |
|---|---|---|---|---|
| Rz POOL | 5'- NNNNNNNN | agaa | NNNN -3' | |
| LIBRARY EXP. A | | | | |
| RzAUCA | 5'- CUAACUUU | agaa | ACUA -3' | HUMAN eIF2γ (13/16) |
| RzGCGU | 5'- UAAUUAUU | agaa | UGCG -3' | |
| RzGACU | 5'- GCGAUCUA | agaa | UCAG -3' | |
| RzUUCG | 5'- AGACCAAA | agaa | GCUU -3' | |
| RzGCCA | 5'- ACAGCCAG | agaa | ACCG -3' | |
| RzGCAU | 5'- UUAAACGC | agaa | UACG -3' | |
| RzAAGC | 5'- UAUUGGCU | agaa | CGAA -3' | |
| RzCGUC | 5'- UCAGCCUC | agaa | CUGC -3' | |
| RzCGUC | 5'- AGCUGGC | agaa | CUGC -3' | |
| RzUUCA | 5'- UUGUUAAU | agaa | ACUU -3' | |
| RzUCGA | 5'- UUCUUAUU | agaa | AGCU -3' | HUMAN eIF2Bγ (19/22) |
| LIBRARY EXP. B | | | | |
| RzAAGG | 5'- UCGCUUAA | agaa | GGAA -3' | |
| RzUCUU | 5'- UUCGUCAA | agaa | UUCU -3' | HUMAN PROTEASOME ALPHA SUBUNIT, PSMA1 (14/16) |
| RzCAGA | 5'- UAACACGU | agaa | AGAC -3' | |
| RzCCCU | 5'- AGCCGAGG | agaa | UCCC -3' | |
| RzGCUC | 5'- CUGUCAAC | agaa | CUCG -3' | |
| RzAGGU | 5'- AUUCAUAU | agaa | UGGA -3' | |
| RzCUAC | 5'- CUUGCGCG | agaa | CAUC -3' | |
| CONTROL Rz | | | | |
| RzGACG | 5'- AGCCGCAU | agaa | GCAG -3' | HUMAN PROTEASOME ALPHA SUBUNIT, PSMA7 (15/16) |
| RzBR1 | 5'- AGGUUGGG | agaa | GCGA -3' | HUMAN HEPATITIS B VIRUS |
| RzGCCA | 5'- AUUGCCAG | agaa | ACCG -3' | HUMAN HEPATITIS C VIRUS |

FIG. 4D

```
      1 GGAGATCGCTGGGAGCGGTTGCGCGTGCGGGGAGCTGAGTTA    42
  TAGCTGTGACTTCTGCCCTGCCAGGCCGCACACAGCGGTCTGACCCGGTTTGGTTTGTAA  102
       ATGGAATTTCAAGCAGTAGTGATGGCAGTAGGTGGAGGATCTCGGATGACAGACCTAACT  162
   1    M  E  F  Q  A  V  V  M  A  V  G  G  G  S  R  M  T  D  L  T
       TCCAGCATTCCCAAACCTCTGCTTCCAGTTGGGAACAAACCTTTAATTTGGTACCCATTG  222
  21    S  S  I  P  K  P  L  L  P  V  G  N  K  P  L  I  W  Y  P  L
       AACCTGCTTGAGCGTGTTGGATTTGAAGAAGTCATTGTGGTTACAACCAGGGATGTTCAA  282
  41    N  L  L  E  R  V  G  F  E  E  V  I  V  V  T  T  R  D  V  Q
       AAGGCTCTATGTGCAGAATTCAAGATGAAAATGAAGCCAGATATTGTGTGTATTCCTGAT  342
  61    K  A  L  C  A  E  F  K  M  K  M  K  P  D  I  V  C  I  P  D
       GACGCTGACATGGGAACTGCAGATTCTTTGCGCTACATATATCCAAAACTTAAGACAGAT  402
  81    D  A  D  M  G  T  A  D  S  L  R  Y  I  Y  P  K  L  K  T  D
       GTGCTGGTGCTGAGCTGTGATCTGATAACAGACGTTGCCTTACATGAGGTTGTGGACCTG  462
 101    V  L  V  L  S  C  D  L  I  T  D  V  A  L  H  E  V  V  D  L
       TTTAGAGCTTATGATGCATCACTTGCTATGTTGATGAGAAAAGGCCAAGATAGCATAGAA  522
 121    F  R  A  Y  D  A  S  L  A  M  L  M  R  K  G  Q  D  S  I  E
       CCTGTTCCCGGTCAAAAGGGGAAAAAAAAAGCAGTGGAGCAGCGTGACTTCATTGGAGTG  582
 141    P  V  P  G  Q  K  G  K  K  K  A  V  E  Q  R  D  F  I  G  V
       GACAGCACAGGAAAGAGGCTGCTCTTCATGGCTAATGAAGCAGACTTGGATGAAGAGCTG  642
 161    D  S  T  G  K  R  L  L  F  M  A  N  E  A  D  L  D  E  E  L
       GTCATTAAGGGATCCATCCTACAGAAGCATCCTAGAATACGTTTCCACACGGGTCTTGTG  702
 181    V  I  K  G  S  I  L  Q  K  H  P  R  I  R  F  H  T  G  L  V
       GATGCCCACCTCTACTGTTTGAAAAAATACATCGTGGATTTCCTAATGGAAAATGGGTCA  762
 201    D  A  H  L  Y  C  L  K  K  Y  I  V  D  F  L  M  E  N  G  S
       ATAACTTCTATCCGGAGTGAACTGATTCCATATTTAGTGAGAAAACAGTTTTCCTCAGCT  822
 221    I  T  S  I  R  S  E  L  I  P  Y  L  V  R  K  Q  F  S  S  A
       TCCTCACAACAGGGACAAGAAGAAAAAGAGGAGGATCTAAAGAAAAAGGAGCTGAAGTCC  882
 241    S  S  Q  Q  G  Q  E  E  K  E  E  D  L  K  K  K  E  L  K  S
       TTAGATATCTACAGTTTTATAAAAGAAGCCAATACACTGAACCTGGCTCCCTATGATGCC  942
 261    L  D  I  Y  S  F  I  K  E  A  N  T  L  N  L  A  P  Y  D  A
       TGCTGGAATGCCTGTCGAGGAGACAGGTGGGAAGACTTGTCCAGATCACAGGTGCGCTGC 1002
 281    C  W  N  A  C  R  G  D  R  W  E  D  L  S  R  S  Q  V  R  C
       TATGTCCACATCATGAAAGAGGGGCTCTGCTCTCGAGTGAGCACACTGGGACTCTACATG 1062
 301    Y  V  H  I  M  K  E  G  L  C  S  R  V  S  T  L  G  L  Y  M
       GAAGCAAACAGACAGGTGCCCAAATTGCTGTCTGCTCTCTGTCCAGAAGAACCACCAGTC 1122
 321    E  A  N  R  Q  V  P  K  L  L  S  A  L  C  P  E  E  P  P  V
       CATTCGTCAGCCCAGATTGTCAGCAAACACCTGGTTGGAGTTGACAGCCTCATTGGGCCA 1182
 341    H  S  S  A  Q  I  V  S  K  H  L  V  G  V  D  S  L  I  G  P
       GAGACACAGATTGGAGAGAAGTCATCCATTAAGCGCTCAGTCATTGGCTCATCCTGTCTC 1242
 361    E  T  Q  I  G  E  K  S  S  I  K  R  S  V  I  G  S  S  C  L
       ATAAAAGATAGAGTGACTATTACCAATTGCCTTCTCATGAACTCAGTCACTGTGGAGGAA 1302
 381    I  K  D  R  V  T  I  T  N  C  L  L  M  N  S  V  T  V  E  E
       GGAAGCAATATCCAAGGCAGTGTCATCTGCAACAATGCTGTGATCGAGAAGGGTGCAGAC 1362
 401    G  S  N  I  Q  G  S  V  I  C  N  N  A  V  I  E  K  G  A  D
       ATCAAGGACTGCTTGATTGGAAGTGGCCAGAGGATTGAAGCCAAAGCTAAACGAGTGAAT 1422
 421    I  K  D  C  L  I  G  S  G  Q  R  I  E  A  K  A  K  R  V  N
       GAGGTGATCGTGGGGAATGACCAGCTCATGGAGATCTGAGTTCTGAGCAAGTCAGACTCC 1482
 441    E  V  I  V  G  N  D  Q  L  M  E  I  *
       TTCCTTTTGGCCTCCAAAGCCACAGATGTTGGCCGGCCCACCTGTTTAACTCTGTATTTA 1542
       TTTCCCAATAAAGAAGGGCTTCCAAAGGTA 1602
```

FIG. 5A

| | | |
|---|---|---|
| human eIF2Bγ | MEFQAVVMAVGGGSRMTDLTSSIPKPLLPVGNKPLIWYPLNLLERVGFEE | 50 |
| | ||||||||||||||||||||||||||||||||||||||||||||||||| | |
| rat eIF2Bγ | MEFQAVVMAVGGGSRMTDLTSSIPKPLLPVGNKPLIWYPLNLLERVGFEE | 50 |
| human eIF2Bγ | VIVVTTRDVQKALCAEFKMKMKPDIVCIPDDADMGTADSLRYIYPKLKTD | 100 |
| | |||||| ||||||||||||| |||||||| ||||||||||| ||||||| | |
| rat eIF2Bγ | VIVVTTKDVQKALCAEFKMKLKPDIVCIPDEADMGTADSLRHIYPKLKTD | 100 |
| human eIF2Bγ | VLVLSCDLITDVALHEVVDLFRAYDASLAMLMRKGQDSIEPVPGQKGKKK | 150 |
| | |||| ||||||||||||||||||||||||||||||| | ||||||||||| | |
| rat eIF2Bγ | VLVLGCDLITDVALHEVVDLFRAYDASLAMLMRKGQESTEPVPGQKGKKK | 150 |
| human eIF2Bγ | AVEQRDFIGVDSTGKRLLFMANEADLDEELVIKGSILQKHPRIRFHTGLV | 200 |
| | ||||||||||||||||||||||||||||||||||||||||||| |||| | |
| rat eIF2Bγ | TVEQRDFIGVDSTGKRLLFMANEADLDEELVIKGSILQKHPRIHFQTGLV | 200 |
| human eIF2Bγ | DAHLYCLKKYIVDFLMENGSITSIRSELIPYLVRKQFSSASSQQGQEEKE | 250 |
| | |||||||||| ||||||| ||||||||||||||||||||||||| || || | |
| rat eIF2Bγ | DAHLYCLKKYVVDFLMENKSITSIRSELIPYLVRKQFSSASSQQRQEDKE | 250 |
| human eIF2Bγ | EDLKKKELKSLDIYSFIKEANTLNLAPYDACWNACRGDRWEDLSRSQVRC | 300 |
| | ||||||| |||||||||| ||| ||||||||||| | | ||||||||||| | |
| rat eIF2Bγ | EDLKKKEPKSLDIYSFIKKDNTLTLAPYDACWNAFRRDKWEDLSRSQVRC | 300 |
| human eIF2Bγ | YVHIMKEGLCSRVSTLGLYMEANRQVPKLLSALCPEEPPVHSSAQIVSKH | 350 |
| | ||||||||||||||||||||||||||||||||| ||||| | |||| || | |
| rat eIF2Bγ | YVHIMKEGLCSRVSTLGLYMEANRQVPKLLSVLCPEESMIHPSAQIANKH | 350 |
| human eIF2Bγ | LVGVDSLIGPETQIGEKSSIKRSVIGSSCLIKDRVTITNCLLMNSVTVEE | 400 |
| | | | |||||| || ||||||||||||||| | |||| ||||||||||| | | |
| rat eIF2Bγ | LIGADSLIGSDTQVGEKSSIKRSVIGSSCVIRDRVTVTNCLLMNSVTVGE | 400 |
| human eIF2Bγ | GSNIQGSVICNNAVIEKGADIKDCLIGSGQRIEAKAKRVNEVIVGNDQLM | 450 |
| | || | |||| |||| | || | |||||||||||||||| ||||||||||| | |
| rat eIF2Bγ | GSSIHGSVIFNNAVVEAGAEIRDCLIGSGQRIEAKAKRMNEVIVGNDQLM | 450 |
| human eIF2Bγ | EI*.. 452 | |
| | || | |
| rat eIF2Bγ | EI*.. 452 | |

*FIG. 5B*

| | CONTROL 1 | HCV6 2 | TV1 3 | TV2 4 | TV3 5 | TV4 6 | TV5 7 |
|---|---|---|---|---|---|---|---|
| COLONIES / 150 CM² | 58 | 96.0 | 606 | 682 | 976 | 880 | 560 |
| FOLD ENRICHMENT | - | 16.6 | 10.5 | 11.8 | 16.8 | 15.2 | 9.7 |
| RELATIVE eIF2Bγ RNA EXPRESSION (% OF CONTROL) | 100 | 78 | n.d | 85 | 103 | 81 | 80 |
| | 100 | 256 | 144 | 202 | 166 | 189 | 131 |

SEQUENCE LISTING

<160> NUMBER OF SEQ ID NOS: 144

<210> SEQ ID NO 1
<211> LENGTH: 1572
<212> TYPE: DNA
<213> ORGANISM: Homo sapiens
<220> FEATURE:
<221> NAME/KEY: CDS
<222> LOCATION: (103)..(1458)

<400> SEQUENCE: 1

```
ggagatcgct gggagcggtt gcgcgtgcgg ggagctgagt tatagctgtg acttctgccc      60
tgccaggccg cacacagcgg tctgacccgg tttggtttgt aa atg gaa ttt caa        114
                                                Met Glu Phe Gln
                                                  1 gca gta gtg atg gca gta ggt gga gga tct cgg atg aca gac cta act       162
Ala Val Val Met Ala Val Gly Gly Gly Ser Arg Met Thr Asp Leu Thr
  5                  10                  15                  20 tcc agc att ccc aaa cct ctg ctt cca gtt ggg aac aaa cct tta att       210
Ser Ser Ile Pro Lys Pro Leu Leu Pro Val Gly Asn Lys Pro Leu Ile
                 25                  30                  35 tgg tac cca ttg aac ctg ctt gag cgt gtt gga ttt gaa gaa gtc att       258
Trp Tyr Pro Leu Asn Leu Leu Glu Arg Val Gly Phe Glu Glu Val Ile
             40                  45                  50 gtg gtt aca acc agg gat gtt caa aag gct cta tgt gca gaa ttc aag       306
Val Val Thr Thr Arg Asp Val Gln Lys Ala Leu Cys Ala Glu Phe Lys
         55                  60                  65 atg aaa atg aag cca gat att gtg tgt att cct gat gac gct gac atg       354
Met Lys Met Lys Pro Asp Ile Val Cys Ile Pro Asp Asp Ala Asp Met
 70                  75                  80 gga act gca gat tct ttg cgc tac ata tat cca aaa ctt aag aca gat       402
Gly Thr Ala Asp Ser Leu Arg Tyr Ile Tyr Pro Lys Leu Lys Thr Asp
 85                  90                  95                 100 gtg ctg gtg ctg agc tgt gat ctg ata aca gac gtt gcc tta cat gag       450
Val Leu Val Leu Ser Cys Asp Leu Ile Thr Asp Val Ala Leu His Glu
                105                 110                 115 gtt gtg gac ctg ttt aga gct tat gat gca tca ctt gct atg ttg atg       498
Val Val Asp Leu Phe Arg Ala Tyr Asp Ala Ser Leu Ala Met Leu Met
            120                 125                 130 aga aaa ggc caa gat agc ata gaa cct gtt ccc ggt caa aag ggg aaa       546
Arg Lys Gly Gln Asp Ser Ile Glu Pro Val Pro Gly Gln Lys Gly Lys
        135                 140                 145 aaa aaa gca gtg gag cag cgt gac ttc att gga gtg gac agc aca gga       594
Lys Lys Ala Val Glu Gln Arg Asp Phe Ile Gly Val Asp Ser Thr Gly
    150                 155                 160 aag agg ctg ctc ttc atg gct aat gaa gca gac ttg gat gaa gag ctg       642
Lys Arg Leu Leu Phe Met Ala Asn Glu Ala Asp Leu Asp Glu Glu Leu
165                 170                 175                 180 gtc att aag gga tcc atc cta cag aag cat cct aga ata cgt ttc cac       690
Val Ile Lys Gly Ser Ile Leu Gln Lys His Pro Arg Ile Arg Phe His
                185                 190                 195 acg ggt ctt gtg gat gcc cac ctc tac tgt ttg aaa aaa tac atc gtg       738
Thr Gly Leu Val Asp Ala His Leu Tyr Cys Leu Lys Lys Tyr Ile Val
            200                 205                 210 gat ttc cta atg gaa aat ggg tca ata act tct atc cgg agt gaa ctg       786
Asp Phe Leu Met Glu Asn Gly Ser Ile Thr Ser Ile Arg Ser Glu Leu
        215                 220                 225 att cca tat tta gtg aga aaa cag ttt tcc tca gct tcc tca caa cag       834
Ile Pro Tyr Leu Val Arg Lys Gln Phe Ser Ser Ala Ser Ser Gln Gln
```

-continued

```
                 230                 235                 240
gga caa gaa gaa aaa gag gag gat cta aag aaa aag gag ctg aag tcc    882
Gly Gln Glu Glu Lys Glu Glu Asp Leu Lys Lys Lys Glu Leu Lys Ser
245                 250                 255                 260 tta gat atc tac agt ttt ata aaa gaa gcc aat aca ctg aac ctg gct    930
Leu Asp Ile Tyr Ser Phe Ile Lys Glu Ala Asn Thr Leu Asn Leu Ala
            265                 270                 275 ccc tat gat gcc tgc tgg aat gcc tgt cga gga gac agg tgg gaa gac    978
Pro Tyr Asp Ala Cys Trp Asn Ala Cys Arg Gly Asp Arg Trp Glu Asp
        280                 285                 290 ttg tcc aga tca cag gtg cgc tgc tat gtc cac atc atg aaa gag ggg   1026
Leu Ser Arg Ser Gln Val Arg Cys Tyr Val His Ile Met Lys Glu Gly
    295                 300                 305 ctc tgc tct cga gtg agc aca ctg gga ctc tac atg gaa gca aac aga   1074
Leu Cys Ser Arg Val Ser Thr Leu Gly Leu Tyr Met Glu Ala Asn Arg
310                 315                 320 cag gtg ccc aaa ttg ctg tct gct ctc tgt cca gaa gaa cca cca gtc   1122
Gln Val Pro Lys Leu Leu Ser Ala Leu Cys Pro Glu Glu Pro Pro Val
325                 330                 335                 340 cat tcg tca gcc cag att gtc agc aaa cac ctg gtt gga gtt gac agc   1170
His Ser Ser Ala Gln Ile Val Ser Lys His Leu Val Gly Val Asp Ser
            345                 350                 355 ctc att ggg cca gag aca cag att gga gag aag tca tcc att aag cgc   1218
Leu Ile Gly Pro Glu Thr Gln Ile Gly Glu Lys Ser Ser Ile Lys Arg
        360                 365                 370 tca gtc att ggc tca tcc tgt ctc ata aaa gat aga gtg act att acc   1266
Ser Val Ile Gly Ser Ser Cys Leu Ile Lys Asp Arg Val Thr Ile Thr
    375                 380                 385 aat tgc ctt ctc atg aac tca gtc act gtg gag gaa gga agc aat atc   1314
Asn Cys Leu Leu Met Asn Ser Val Thr Val Glu Glu Gly Ser Asn Ile
390                 395                 400 caa ggc agt gtc atc tgc aac aat gct gtg atc gag aag ggt gca gac   1362
Gln Gly Ser Val Ile Cys Asn Asn Ala Val Ile Glu Lys Gly Ala Asp
405                 410                 415                 420 atc aag gac tgc ttg att gga agt ggc cag agg att gaa gcc aaa gct   1410
Ile Lys Asp Cys Leu Ile Gly Ser Gly Gln Arg Ile Glu Ala Lys Ala
            425                 430                 435 aaa cga gtg aat gag gtg atc gtg ggg aat gac cag ctc atg gag atc   1458
Lys Arg Val Asn Glu Val Ile Val Gly Asn Asp Gln Leu Met Glu Ile
        440                 445                 450 tgagttctga gcaagtcaga ctccttcctt ttggcctcca agccacaga tgttggccgg   1518 cccacctgtt taactctgta tttatttccc aataaagaag ggcttccaaa ggta         1572

<210> SEQ ID NO 2
<211> LENGTH: 452
<212> TYPE: PRT
<213> ORGANISM: Homo sapiens

<400> SEQUENCE: 2

Met Glu Phe Gln Ala Val Val Met Ala Val Gly Gly Gly Ser Arg Met
1               5                   10                  15

Thr Asp Leu Thr Ser Ser Ile Pro Lys Pro Leu Leu Pro Val Gly Asn
            20                  25                  30

Lys Pro Leu Ile Trp Tyr Pro Leu Asn Leu Leu Glu Arg Val Gly Phe
        35                  40                  45

Glu Glu Val Ile Val Val Thr Thr Arg Asp Val Gln Lys Ala Leu Cys
    50                  55                  60

Ala Glu Phe Lys Met Lys Met Lys Pro Asp Ile Val Cys Ile Pro Asp
```

```
              65                  70                  75                  80
Asp Ala Asp Met Gly Thr Ala Asp Ser Leu Arg Tyr Ile Tyr Pro Lys
                     85                  90                  95

Leu Lys Thr Asp Val Leu Val Leu Ser Cys Asp Leu Ile Thr Asp Val
                100                 105                 110

Ala Leu His Glu Val Val Asp Leu Phe Arg Ala Tyr Asp Ala Ser Leu
                115                 120                 125

Ala Met Leu Met Arg Lys Gly Gln Asp Ser Ile Glu Pro Val Pro Gly
130                 135                 140

Gln Lys Gly Lys Lys Ala Val Glu Gln Arg Asp Phe Ile Gly Val
145                 150                 155                 160

Asp Ser Thr Gly Lys Arg Leu Leu Phe Met Ala Asn Glu Ala Asp Leu
                165                 170                 175

Asp Glu Glu Leu Val Ile Lys Gly Ser Ile Leu Gln Lys His Pro Arg
                180                 185                 190

Ile Arg Phe His Thr Gly Leu Val Asp Ala His Leu Tyr Cys Leu Lys
                195                 200                 205

Lys Tyr Ile Val Asp Phe Leu Met Glu Asn Gly Ser Ile Thr Ser Ile
210                 215                 220

Arg Ser Glu Leu Ile Pro Tyr Leu Val Arg Lys Gln Phe Ser Ser Ala
225                 230                 235                 240

Ser Ser Gln Gln Gly Gln Glu Glu Lys Glu Glu Asp Leu Lys Lys Lys
                245                 250                 255

Glu Leu Lys Ser Leu Asp Ile Tyr Ser Phe Ile Lys Glu Ala Asn Thr
                260                 265                 270

Leu Asn Leu Ala Pro Tyr Asp Ala Cys Trp Asn Ala Cys Arg Gly Asp
                275                 280                 285

Arg Trp Glu Asp Leu Ser Arg Ser Gln Val Arg Cys Tyr Val His Ile
                290                 295                 300

Met Lys Glu Gly Leu Cys Ser Arg Val Ser Thr Leu Gly Leu Tyr Met
305                 310                 315                 320

Glu Ala Asn Arg Gln Val Pro Lys Leu Leu Ser Ala Leu Cys Pro Glu
                325                 330                 335

Glu Pro Pro Val His Ser Ser Ala Gln Ile Val Ser Lys His Leu Val
                340                 345                 350

Gly Val Asp Ser Leu Ile Gly Pro Glu Thr Gln Ile Gly Glu Lys Ser
                355                 360                 365

Ser Ile Lys Arg Ser Val Ile Gly Ser Ser Cys Leu Ile Lys Asp Arg
                370                 375                 380

Val Thr Ile Thr Asn Cys Leu Leu Met Asn Ser Val Thr Val Glu Glu
385                 390                 395                 400

Gly Ser Asn Ile Gln Gly Ser Val Ile Cys Asn Asn Ala Val Ile Glu
                405                 410                 415

Lys Gly Ala Asp Ile Lys Asp Cys Leu Ile Gly Ser Gly Gln Arg Ile
                420                 425                 430

Glu Ala Lys Ala Lys Arg Val Asn Glu Val Ile Val Gly Asn Asp Gln
                435                 440                 445

Leu Met Glu Ile
        450

<210> SEQ ID NO 3
<211> LENGTH: 18
<212> TYPE: DNA
<213> ORGANISM: Homo sapiens
```

```
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (1)..(5)
<223> OTHER INFORMATION: a, c, t (u) or g
<221> NAME/KEY: modified_base
<222> LOCATION: (9)..(18)
<223> OTHER INFORMATION: a, c, t (u) or g

<400> SEQUENCE: 3
nnnnngucnn nnnnnnnn                                               18

<210> SEQ ID NO 4
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t  for DNA
<221> NAME/KEY: modified_base
<222> LOCATION: (1)..(5)
<223> OTHER INFORMATION: a, c, t (u) or g
<221> NAME/KEY: modified_base
<222> LOCATION: (9)..(16)
<223> OTHER INFORMATION: a, c, t (u) or g

<400> SEQUENCE: 4
nnnnnguann nnnnnn                                                 16

<210> SEQ ID NO 5
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t  for DNA
<221> NAME/KEY: modified_base
<222> LOCATION: (1)..(8)
<223> OTHER INFORMATION: a, c, t (u) or g
<221> NAME/KEY: modified_base
<222> LOCATION: (13)..(16)
<223> OTHER INFORMATION: a, c, t (u) or g

<400> SEQUENCE: 5
nnnnnnnnag aannnn                                                 16

<210> SEQ ID NO 6
<211> LENGTH: 16
<212> TYPE: RNA
<213> ORGANISM: Homo sapiens

<400> SEQUENCE: 6
cuaacuuuag aaacua                                                 16

<210> SEQ ID NO 7
<211> LENGTH: 16
<212> TYPE: RNA
<213> ORGANISM: Homo sapiens

<400> SEQUENCE: 7
uaauuauuag aaugcg                                                 16

<210> SEQ ID NO 8
<211> LENGTH: 16
<212> TYPE: RNA
<213> ORGANISM: Homo sapiens

<400> SEQUENCE: 8
```

```
gcgaucuaag aaucag                                               16

<210> SEQ ID NO 9
<211> LENGTH: 16
<212> TYPE: RNA
<213> ORGANISM: Homo sapiens

<400> SEQUENCE: 9
agaccaaaag aagcuu                                               16

<210> SEQ ID NO 10
<211> LENGTH: 16
<212> TYPE: RNA
<213> ORGANISM: Homo sapiens

<400> SEQUENCE: 10
acagccagag aaaccg                                               16

<210> SEQ ID NO 11
<211> LENGTH: 16
<212> TYPE: RNA
<213> ORGANISM: Homo sapiens

<400> SEQUENCE: 11
uuaaacgcag aauacg                                               16

<210> SEQ ID NO 12
<211> LENGTH: 16
<212> TYPE: RNA
<213> ORGANISM: Homo sapiens

<400> SEQUENCE: 12
uauuggcuag aacgaa                                               16

<210> SEQ ID NO 13
<211> LENGTH: 16
<212> TYPE: RNA
<213> ORGANISM: Homo sapiens

<400> SEQUENCE: 13
ucagccucag aacugc                                               16

<210> SEQ ID NO 14
<211> LENGTH: 15
<212> TYPE: RNA
<213> ORGANISM: Homo sapiens

<400> SEQUENCE: 14
agcuggcaga acugc                                                15

<210> SEQ ID NO 15
<211> LENGTH: 16
<212> TYPE: RNA
<213> ORGANISM: Homo sapiens

<400> SEQUENCE: 15
uuguuaauag aaacuu                                               16

<210> SEQ ID NO 16
<211> LENGTH: 16
<212> TYPE: RNA
<213> ORGANISM: Homo sapiens
```

-continued

```
<400> SEQUENCE: 16
uucuuauuag aaagcu                                                     16

<210> SEQ ID NO 17
<211> LENGTH: 16
<212> TYPE: RNA
<213> ORGANISM: Homo sapiens

<400> SEQUENCE: 17
ucgcuuaaag aaggaa                                                     16

<210> SEQ ID NO 18
<211> LENGTH: 16
<212> TYPE: RNA
<213> ORGANISM: Homo sapiens

<400> SEQUENCE: 18
uucgucaaag aauucu                                                     16

<210> SEQ ID NO 19
<211> LENGTH: 16
<212> TYPE: RNA
<213> ORGANISM: Homo sapiens

<400> SEQUENCE: 19
uaacacguag aaagac                                                     16

<210> SEQ ID NO 20
<211> LENGTH: 16
<212> TYPE: RNA
<213> ORGANISM: Homo sapiens

<400> SEQUENCE: 20
agccgaggag aauccc                                                     16

<210> SEQ ID NO 21
<211> LENGTH: 16
<212> TYPE: RNA
<213> ORGANISM: Homo sapiens

<400> SEQUENCE: 21
cugucaacag aacucg                                                     16

<210> SEQ ID NO 22
<211> LENGTH: 16
<212> TYPE: RNA
<213> ORGANISM: Homo sapiens

<400> SEQUENCE: 22
auucauauag aaugga                                                     16

<210> SEQ ID NO 23
<211> LENGTH: 16
<212> TYPE: RNA
<213> ORGANISM: Homo sapiens

<400> SEQUENCE: 23
cuugcgcgag aacauc                                                     16

<210> SEQ ID NO 24
<211> LENGTH: 16
<212> TYPE: RNA
<213> ORGANISM: Homo sapiens
```

```
<400> SEQUENCE: 24
agccgcauag aagcag                                                   16

<210> SEQ ID NO 25
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 25
uagungucaa aguuag                                                   16

<210> SEQ ID NO 26
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: n = a, c, t(u) or g

<400> SEQUENCE: 26
cgcangucaa uaauua                                                   16

<210> SEQ ID NO 27
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 27
cugangucua gaucgc                                                   16

<210> SEQ ID NO 28
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 28
aagcngucuu uggucu                                                   16

<210> SEQ ID NO 29
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
```

<223> OTHER INFORMATION: a, c, t (u) or g

<400> SEQUENCE: 29
cggunguccu ggcugu                                                    16

<210> SEQ ID NO 30
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (12)
<223> OTHER INFORMATION: a, c, t (u) or g

<400> SEQUENCE: 30
cguangucgc guuuaa                                                    16

<210> SEQ ID NO 31
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 31
uucgngucag ccaaua                                                    16

<210> SEQ ID NO 32
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 32
gcagngucga ggcuga                                                    16

<210> SEQ ID NO 33
<211> LENGTH: 15
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 33
gcangucugc cagcu                                                     15

<210> SEQ ID NO 34
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base

```
<222> LOCATION: (5)
<223> OTHER INFORMATION: a, c, t (u) or g

<400> SEQUENCE: 34
aagungucau uaacaa                                                16

<210> SEQ ID NO 35
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 35
agcungucaa uaagaa                                                16

<210> SEQ ID NO 36
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 36
uuccngucuu aagcga                                                16

<210> SEQ ID NO 37
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 37
agaangucuu gacgaa                                                16

<210> SEQ ID NO 38
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 38
gucungucac guguua                                                16

<210> SEQ ID NO 39
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
```

```
<221> NAME/KEY: modified_base
<222> LOCATION: (5)
<223> OTHER INFORMATION: a, c, t (u) or g

<400> SEQUENCE: 39
ggganguccc ucggcu                                                          16

<210> SEQ ID NO 40
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 40
cgagngucgu ugacag                                                          16

<210> SEQ ID NO 41
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 41
uccangucau augaau                                                          16

<210> SEQ ID NO 42
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 42 gaugnuccg cgcaag                                                           16

<210> SEQ ID NO 43
<211> LENGTH: 16
<212> TYPE: DNA
<213> ORGANISM: Homo sapiens
<220> FEATURE:
<223> OTHER INFORMATION: Description of Combined DNA/RNA Molecule: DNA
      or RNA where u can be u for RNA or t for DNA
<221> NAME/KEY: modified_base
<222> LOCATION: (5)
<223> OTHER INFORMATION: a, c, t (u) or g

<400> SEQUENCE: 43
cugcngucau gcggcu                                                          16

<210> SEQ ID NO 44
<211> LENGTH: 78
<212> TYPE: DNA
<213> ORGANISM: Artificial Sequence
<220> FEATURE:
<221> NAME/KEY: modified_base
```

```
<222> LOCATION: (41)..(44)
<223> OTHER INFORMATION: a, c, t or g
<221> NAME/KEY: modified_base
<222> LOCATION: (49)..(56)
<223> OTHER INFORMATION: a, c, t or g
<223> OTHER INFORMATION: Description of Artificial Sequence: synthetic
      primer

<400> SEQUENCE: 44
cgcgtaccag gtaatatacc acaacgtgtg tttctctggt nnnnttctnn nnnnnnggat    60
cctgtttccg cccggttt                                                 78

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: synthetic
      primer

<400> SEQUENCE: 45
cgttgtggta tattacctgg ta                                            22

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 46
cgaaaccggg cggaaacagg                                               20

<210> SEQ ID NO 47
<211> LENGTH: 51
<212> TYPE: DNA
<213> ORGANISM: Artificial Sequence
<220> FEATURE:
<223> OTHER INFORMATION: Description of Artificial Sequence: synthetic
      primer

<400> SEQUENCE: 47
agctggcaga actgcaccag agaaacacac gttgtggtac attacctggt a            51

<210> SEQ ID NO 48
<211> LENGTH: 52
<212> TYPE: DNA
<213> ORGANISM: Artificial Sequence
<220> FEATURE:
<223> OTHER INFORMATION: Description of Artificial Sequence: synthetic
      primer

<400> SEQUENCE: 48
ttcgtcaaag aattctacca gagaaacaca cgttgtggta cattacctgg ta           52

<210> SEQ ID NO 49
<211> LENGTH: 52
<212> TYPE: DNA
<213> ORGANISM: Artificial Sequence
<220> FEATURE:
<223> OTHER INFORMATION: Description of Artificial Sequence: synthetic
      primer

<400> SEQUENCE: 49
gcgatctaag aatcagacca gagaaacaca cgttgtggta cattacctgg ta           52
```

```
<210> SEQ ID NO 50
<211> LENGTH: 52
<212> TYPE: DNA
<213> ORGANISM: Artificial Sequence
<220> FEATURE:
<223> OTHER INFORMATION: Description of Artificial Sequence: synthetic
      primer

<400> SEQUENCE: 50
ctaactttag aaactaacca gagaaacaca cgttgtggta cattacctgg ta         52

<210> SEQ ID NO 51
<211> LENGTH: 52
<212> TYPE: DNA
<213> ORGANISM: Artificial Sequence
<220> FEATURE:
<223> OTHER INFORMATION: Description of Artificial Sequence: synthetic
      primer

<400> SEQUENCE: 51
cttgcgcgag aacatcacca gagaaacaca cgttgtggta cattacctgg ta         52

<210> SEQ ID NO 52
<211> LENGTH: 52
<212> TYPE: DNA
<213> ORGANISM: Artificial Sequence
<220> FEATURE:
<223> OTHER INFORMATION: Description of Artificial Sequence: synthetic
      primer

<400> SEQUENCE: 52
ttcttattag aaagctacca gagaaacaca cgttgtggta cattacctgg ta         52

<210> SEQ ID NO 53
<211> LENGTH: 52
<212> TYPE: DNA
<213> ORGANISM: Artificial Sequence
<220> FEATURE:
<223> OTHER INFORMATION: Description of Artificial Sequence: synthetic
      primer

<400> SEQUENCE: 53
tcgcttaaag aaggaaacca gagaaacaca cgttgtggta cattacctgg ta         52

<210> SEQ ID NO 54
<211> LENGTH: 52
<212> TYPE: DNA
<213> ORGANISM: Artificial Sequence
<220> FEATURE:
<223> OTHER INFORMATION: Description of Artificial Sequence: synthetic
      primer

<400> SEQUENCE: 54
agccgaggag aatcccacca gagaaacaca cgttgtggta cattacctgg ta         52

<210> SEQ ID NO 55
<211> LENGTH: 52
<212> TYPE: DNA
<213> ORGANISM: Artificial Sequence
<220> FEATURE:
<223> OTHER INFORMATION: Description of Artificial Sequence: synthetic
      primer

<400> SEQUENCE: 55
agccgcatag aagcagacca gagaaacaca cgttgtggta cattacctgg ta         52
```

<210> SEQ ID NO 56
<211> LENGTH: 52
<212> TYPE: DNA
<213> ORGANISM: Artificial Sequence
<220> FEATURE:
<223> OTHER INFORMATION: Description of Artificial Sequence: synthetic primer

<400> SEQUENCE: 56
taattattag aatgcgacca gagaaacaca cgttgtggta cattacctgg ta     52

<210> SEQ ID NO 57
<211> LENGTH: 52
<212> TYPE: DNA
<213> ORGANISM: Artificial Sequence
<220> FEATURE:
<223> OTHER INFORMATION: Description of Artificial Sequence: synthetic primer

<400> SEQUENCE: 57
agaccaaaag aagcttacca gagaaacaca cgttgtggta cattacctgg ta     52

<210> SEQ ID NO 58
<211> LENGTH: 52
<212> TYPE: DNA
<213> ORGANISM: Artificial Sequence
<220> FEATURE:
<223> OTHER INFORMATION: Description of Artificial Sequence: synthetic primer

<400> SEQUENCE: 58
acagccagag aaaccgacca gagaaacaca cgttgtggta cattacctgg ta     52

<210> SEQ ID NO 59
<211> LENGTH: 52
<212> TYPE: DNA
<213> ORGANISM: Artificial Sequence
<220> FEATURE:
<223> OTHER INFORMATION: Description of Artificial Sequence: synthetic primer

<400> SEQUENCE: 59
ttaaacgcag aatacgacca gagaaacaca cgttgtggta cattacctgg ta     52

<210> SEQ ID NO 60
<211> LENGTH: 52
<212> TYPE: DNA
<213> ORGANISM: Artificial Sequence
<220> FEATURE:
<223> OTHER INFORMATION: Description of Artificial Sequence: synthetic primer

<400> SEQUENCE: 60
tattggctag aacgaaacca gagaaacaca cgttgtggta cattacctgg ta     52

<210> SEQ ID NO 61
<211> LENGTH: 52
<212> TYPE: DNA
<213> ORGANISM: Artificial Sequence
<220> FEATURE:
<223> OTHER INFORMATION: Description of Artificial Sequence: synthetic primer

<400> SEQUENCE: 61
tcagcctcag aactgcacca gagaaacaca cgttgtggta cattacctgg ta     52

<210> SEQ ID NO 62

```
<211> LENGTH: 52
<212> TYPE: DNA
<213> ORGANISM: Artificial Sequence
<220> FEATURE:
<223> OTHER INFORMATION: Description of Artificial Sequence: synthetic
      primer

<400> SEQUENCE: 62
ttgttaatag aaacttacca gagaaacaca cgttgtggta cattacctgg ta         52

<210> SEQ ID NO 63
<211> LENGTH: 52
<212> TYPE: DNA
<213> ORGANISM: Artificial Sequence
<220> FEATURE:
<223> OTHER INFORMATION: Description of Artificial Sequence: synthetic
      primer

<400> SEQUENCE: 63
taacacgtag aaagacacca gagaaacaca cgttgtggta cattacctgg ta         52

<210> SEQ ID NO 64
<211> LENGTH: 52
<212> TYPE: DNA
<213> ORGANISM: Artificial Sequence
<220> FEATURE:
<223> OTHER INFORMATION: Description of Artificial Sequence: synthetic
      primer

<400> SEQUENCE: 64
ctgtcaacag aactcgacca gagaaacaca cgttgtggta cattacctgg ta         52

<210> SEQ ID NO 65
<211> LENGTH: 52
<212> TYPE: DNA
<213> ORGANISM: Artificial Sequence
<220> FEATURE:
<223> OTHER INFORMATION: Description of Artificial Sequence: synthetic
      primer

<400> SEQUENCE: 65
attcatatag aatggaacca gagaaacaca cgttgtggta cattacctgg ta         52

<210> SEQ ID NO 66
<211> LENGTH: 54
<212> TYPE: DNA
<213> ORGANISM: Artificial Sequence
<220> FEATURE:
<223> OTHER INFORMATION: Description of Artificial Sequence: synthetic
      primer

<400> SEQUENCE: 66
ggatgatgaa gacatacaag gagacgacct tccatggata gatccggaaa gcct       54

<210> SEQ ID NO 67
<211> LENGTH: 34
<212> TYPE: DNA
<213> ORGANISM: Artificial Sequence
<220> FEATURE:
<223> OTHER INFORMATION: Description of Artificial Sequence: synthetic
      primer

<400> SEQUENCE: 67
gtcggcatgt cgactattcc tttgccctcg gacg                             34

<210> SEQ ID NO 68
<211> LENGTH: 83
```

-continued

```
<212> TYPE: DNA
<213> ORGANISM: Artificial Sequence
<220> FEATURE:
<223> OTHER INFORMATION: Description of Artificial Sequence: synthetic
      primer

<400> SEQUENCE: 68
cgatcgtaga attcaggtct cgtagaccgt gcaccatggc ttcgtacccc tgccatcaac    60
acgcgtctgc gttcgaccag gct                                            83

<210> SEQ ID NO 69
<211> LENGTH: 40
<212> TYPE: DNA
<213> ORGANISM: Artificial Sequence
<220> FEATURE:
<223> OTHER INFORMATION: Description of Artificial Sequence: synthetic
      primer

<400> SEQUENCE: 69
gtacccgatt atgatctcag ttagcctccc ccatctcccg                          40

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: synthetic
      primer

<400> SEQUENCE: 70
ggcgggacta tggttgctga ctaat                                          25

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: synthetic
      primer

<400> SEQUENCE: 71
ggttatcacg ttcgcctcac acgc                                           24

<210> SEQ ID NO 72
<211> LENGTH: 16
<212> TYPE: RNA
<213> ORGANISM: Homo sapiens

<400> SEQUENCE: 72
agguugggag aagcga                                                    16

<210> SEQ ID NO 73
<211> LENGTH: 16
<212> TYPE: RNA
<213> ORGANISM: Homo sapiens

<400> SEQUENCE: 73
auugccagag aaaccg                                                    16

<210> SEQ ID NO 74
<211> LENGTH: 16
<212> TYPE: DNA
<213> ORGANISM: Artificial Sequence
<220> FEATURE:
<221> NAME/KEY: modified_base
<222> LOCATION: (12)
```

```
<223> OTHER INFORMATION: a, c, t, or g
<223> OTHER INFORMATION: Description of Artificial Sequence: synthetic
      primer

<400> SEQUENCE: 74
ttcttattga cnagct                                                       16

<210> SEQ ID NO 75
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 75
cagcggucug acccgg                                                       16

<210> SEQ ID NO 76
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 76
aagaagucau uguggu                                                       16

<210> SEQ ID NO 77
<211> LENGTH: 15
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 77
cccggucaaa agggg                                                        15

<210> SEQ ID NO 78
<211> LENGTH: 15
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 78
agcuggucau uaggg                                                        15

<210> SEQ ID NO 79
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide
```

```
<400> SEQUENCE: 79 cacggucuu guggau                                                        16

<210> SEQ ID NO 80
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 80
aaugggucaa uaacuu                                                       16

<210> SEQ ID NO 81
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 81
cugaaguccu uagaua                                                       16

<210> SEQ ID NO 82
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 82
ugccugucga ggagac                                                       16

<210> SEQ ID NO 83
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 83
gacuugucca gaucac                                                       16

<210> SEQ ID NO 84
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 84
gcuaugucca caucau                                                       16
```

```
<210> SEQ ID NO 85
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 85
uugcugucug cucucu                                                      16

<210> SEQ ID NO 86
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 86
ucucugucca gaagaa                                                      16

<210> SEQ ID NO 87
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 87
caccagucca uucguc                                                      16

<210> SEQ ID NO 88
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 88
cauucgucag cccaga                                                      16

<210> SEQ ID NO 89
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 89
agauugucag caaaca                                                      16

<210> SEQ ID NO 90
<211> LENGTH: 16
<212> TYPE: DNA
```

<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 90
gagaagucau ccauua                                                   16

<210> SEQ ID NO 91
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 91
gcucagucau uggcuc                                                   16

<210> SEQ ID NO 92
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 92
auccugucuc auaaaa                                                   16

<210> SEQ ID NO 93
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 93
acucagucac ugugga                                                   16

<210> SEQ ID NO 94
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 94
gcagugucau cugcaa                                                   16

<210> SEQ ID NO 95
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA -continued

```
<223> OTHER INFORMATION: Description of Artificial Sequence: synthetic
      oligonucleotide

<400> SEQUENCE: 95
agcaagucag acuccu                                                    16

<210> SEQ ID NO 96
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 96
uucgcgucag gaucuc                                                    16

<210> SEQ ID NO 97
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 97
aauuggucau guagcu                                                    16

<210> SEQ ID NO 98
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 98
ccacagucgu caaagc                                                    16

<210> SEQ ID NO 99
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 99
cagucgucaa agcuau                                                    16

<210> SEQ ID NO 100
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 100
```
auacugucag guucaa                                                   16

<210> SEQ ID NO 101
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 101
aauuagucag acaugu                                                   16

<210> SEQ ID NO 102
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 102
ugacuguccu ggccac                                                   16

<210> SEQ ID NO 103
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 103
agaaagucag gcuaaa                                                   16

<210> SEQ ID NO 104
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 104
cauuugucca agguac                                                   16

<210> SEQ ID NO 105
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 105
uugaugucaa caaacc                                                   16

```
<210> SEQ ID NO 106
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 106
aggcggucuu auugga                                                     16

<210> SEQ ID NO 107
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 107
gugcagucgg agcuuu                                                     16

<210> SEQ ID NO 108
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 108
aagcugucua agaaug                                                     16

<210> SEQ ID NO 109
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 109
ucccugucaa caggag                                                     16

<210> SEQ ID NO 110
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 110
gugcugucaa ggccga                                                     16

<210> SEQ ID NO 111
<211> LENGTH: 16
<212> TYPE: DNA
<213> ORGANISM: Artificial Sequence
```

```
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 111 uugggucag auaaga                                                      16

<210> SEQ ID NO 112
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 112
augaugucac uguuug                                                     16

<210> SEQ ID NO 113
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 113
aguuggucug aaauca                                                     16

<210> SEQ ID NO 114
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 114
uaugcgucag gagugu                                                     16

<210> SEQ ID NO 115
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 115
ccugugucuc gucuug                                                     16

<210> SEQ ID NO 116
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
``` oligonucleotide

<400> SEQUENCE: 116
gucucgucuu guaucu                                                                16

<210> SEQ ID NO 117
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 117
uguuggucuc cuuauu                                                                16

<210> SEQ ID NO 118
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 118
aaccugucca ucugcu                                                                16

<210> SEQ ID NO 119
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 119
cauaugucug aauuua                                                                16

<210> SEQ ID NO 120
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 120
acauggucug cgugcc                                                                16

<210> SEQ ID NO 121
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 121

-continued gaugugucuc cauucc                                              16

<210> SEQ ID NO 122
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 122
ggaaggucuu gaagaa                                              16

<210> SEQ ID NO 123
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 123
agccagucua uauaug                                              16

<210> SEQ ID NO 124
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 124
aaucagucca gaugug                                              16

<210> SEQ ID NO 125
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 125 aaaggucug uauaau                                               16

<210> SEQ ID NO 126
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 126
uaggugucuu uguggu                                              16

<210> SEQ ID NO 127

```
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 127
ucaccgucuu cucgcc                                                    16

<210> SEQ ID NO 128
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 128
aggccgucaa gaaggg                                                    16

<210> SEQ ID NO 129
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 129
aagaagucag uggcca                                                    16

<210> SEQ ID NO 130
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 130
acaacgucug cauggc                                                    16

<210> SEQ ID NO 131
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 131
ggauagucau caacag                                                    16

<210> SEQ ID NO 132
<211> LENGTH: 16
<212> TYPE: DNA
<213> ORGANISM: Artificial Sequence
<220> FEATURE:
```

-continued

```
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 132 acccgucac ugugga                                                   16

<210> SEQ ID NO 133
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 133
cgccagucug aagcag                                                  16

<210> SEQ ID NO 134
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 134
gccaagucag ugcgcg                                                  16

<210> SEQ ID NO 135
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 135
guucagucag guggca                                                  16

<210> SEQ ID NO 136
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 136
uugcugucau gaggcg                                                  16

<210> SEQ ID NO 137
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide
```

-continued

```
<400> SEQUENCE: 137
aaaaugucuu ugcuug                                                        16

<210> SEQ ID NO 138
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 138
gaugagucuc gaugug                                                        16

<210> SEQ ID NO 139
<211> LENGTH: 16
<212> TYPE: DNA
<213> ORGANISM: Artificial Sequence
<220> FEATURE:
<223> OTHER INFORMATION: Description of Combined DNA/RNA Molecule: DNA
      or RNA where u can be u for RNA or t for DNA
<223> OTHER INFORMATION: Description of Artificial Sequence: synthetic
      oligonucleotide

<400> SEQUENCE: 139
ugaguguccu acaaua                                                        16

<210> SEQ ID NO 140
<211> LENGTH: 452
<212> TYPE: PRT
<213> ORGANISM: Rattus norvegicus

<400> SEQUENCE: 140

Met Glu Phe Gln Ala Val Val Met Ala Val Gly Gly Ser Arg Met
 1               5                  10                  15

Thr Asp Leu Thr Ser Ser Ile Pro Lys Pro Leu Leu Pro Val Gly Asn
                20                  25                  30

Lys Pro Leu Ile Trp Tyr Pro Leu Asn Leu Leu Glu Arg Val Gly Phe
            35                  40                  45

Glu Glu Val Ile Val Val Thr Thr Lys Asp Val Gln Lys Ala Leu Cys
        50                  55                  60

Ala Glu Phe Lys Met Lys Leu Lys Pro Asp Ile Val Cys Ile Pro Asp
    65                  70                  75                  80

Glu Ala Asp Met Gly Thr Ala Asp Ser Leu Arg His Ile Tyr Pro Lys
                85                  90                  95

Leu Lys Thr Asp Val Leu Val Leu Gly Cys Asp Leu Ile Thr Asp Val
                100                 105                 110

Ala Leu His Glu Val Val Asp Leu Phe Arg Ala Tyr Asp Ala Ser Leu
            115                 120                 125

Ala Met Leu Met Arg Lys Gly Gln Glu Ser Thr Glu Pro Val Pro Gly
        130                 135                 140

Gln Lys Gly Lys Lys Lys Thr Val Glu Gln Arg Asp Phe Ile Gly Val
    145                 150                 155                 160

Asp Ser Thr Gly Lys Arg Leu Leu Phe Met Ala Asn Glu Ala Asp Leu
                165                 170                 175

Asp Glu Glu Leu Val Ile Lys Gly Ser Ile Leu Gln Lys His Pro Arg
                180                 185                 190
```

```
Ile His Phe Gln Thr Gly Leu Val Asp Ala His Leu Tyr Cys Leu Lys
        195                 200                 205
Lys Tyr Val Val Asp Phe Leu Met Glu Asn Lys Ser Ile Thr Ser Ile
210                 215                 220
Arg Ser Glu Leu Ile Pro Tyr Leu Val Arg Lys Gln Phe Ser Ser Ala
225                 230                 235                 240
Ser Ser Gln Gln Arg Gln Glu Asp Lys Glu Asp Leu Lys Lys Lys
                245                 250                 255
Glu Pro Lys Ser Leu Asp Ile Tyr Ser Phe Ile Lys Lys Asp Asn Thr
        260                 265                 270
Leu Thr Leu Ala Pro Tyr Asp Ala Cys Trp Asn Ala Phe Arg Arg Asp
        275                 280                 285
Lys Trp Glu Asp Leu Ser Arg Ser Gln Val Arg Cys Tyr Val His Ile
        290                 295                 300
Met Lys Glu Gly Leu Cys Ser Arg Val Ser Thr Leu Gly Leu Tyr Met
305                 310                 315                 320
Glu Ala Asn Arg Gln Val Pro Lys Leu Leu Ser Val Leu Cys Pro Glu
                325                 330                 335
Glu Ser Met Ile His Pro Ser Ala Gln Ile Ala Asn Lys His Leu Ile
        340                 345                 350
Gly Ala Asp Ser Leu Ile Gly Ser Asp Thr Gln Val Gly Glu Lys Ser
        355                 360                 365
Ser Ile Lys Arg Ser Val Ile Gly Ser Ser Cys Val Ile Arg Asp Arg
        370                 375                 380
Val Thr Val Thr Asn Cys Leu Leu Met Asn Ser Val Thr Val Gly Glu
385                 390                 395                 400
Gly Ser Ser Ile His Gly Ser Val Ile Phe Asn Asn Ala Val Val Glu
                405                 410                 415
Ala Gly Ala Glu Ile Arg Asp Cys Leu Ile Gly Ser Gly Gln Arg Ile
                420                 425                 430
Glu Ala Lys Ala Lys Arg Met Asn Glu Val Ile Val Gly Asn Asp Gln
        435                 440                 445
Leu Met Glu Ile
    450

<210> SEQ ID NO 141
<211> LENGTH: 52
<212> TYPE: RNA
<213> ORGANISM: Artificial Sequence
<220> FEATURE:
<223> OTHER INFORMATION: Description of Artificial Sequence: Hairpin
      ribozyme
<221> NAME/KEY: modified_base
<222> LOCATION: (1)..(8)
<223> OTHER INFORMATION: a, c, t (u) or g
<221> NAME/KEY: modified_base
<222> LOCATION: (13)..(16)
<223> OTHER INFORMATION: a, c, t (u) or g

<400> SEQUENCE: 141
nnnnnnnnag aannnnacca gagaaacaca cguuguggua uauuaccugg ua          52

<210> SEQ ID NO 142
<211> LENGTH: 52
<212> TYPE: RNA
<213> ORGANISM: Artificial Sequence
<220> FEATURE:
<223> OTHER INFORMATION: Description of Artificial Sequence: Hairpin
      ribozyme
<221> NAME/KEY: modified_base
```

```
<222> LOCATION: (1)..(8)
<223> OTHER INFORMATION: a, c, t (u) or g
<221> NAME/KEY: modified_base
<222> LOCATION: (13)..(16)
<223> OTHER INFORMATION: a, c, t (u) or g

<400> SEQUENCE: 142
nnnnnnnnag aannnnacca gagcgucaca cguuguggua uauuaccugg ua          52

<210> SEQ ID NO 143
<211> LENGTH: 20
<212> TYPE: RNA
<213> ORGANISM: Homo sapiens

<400> SEQUENCE: 143
agcuggucau uaagggaucc                                              20

<210> SEQ ID NO 144
<211> LENGTH: 22
<212> TYPE: RNA
<213> ORGANISM: Artificial Sequence
<220> FEATURE:
<223> OTHER INFORMATION: Description of Artificial Sequence: Hairpin
      ribozyme

<400> SEQUENCE: 144
ggauccuucu uauuagaaag cu                                           22
```

CELLULAR REGULATORS OF INFECTIOUS AGENTS AND METHODS OF USE

BACKGROUND OF THE INVENTION

This invention relates generally to infectious diseases, and more specifically to methods of identifying cellular regulators essential in the pathogenesis of infectious agents.

Infectious diseases are a serious cause of death and debilitation in the United States and particularly in the non-industrialized populations of the world. In particular, Hepatitis C virus (HCV) is the major cause of non-A, non-B hepatitis, which is also a serious worldwide health problem. Approximately 1% to 2% of the world population is infected with HCV. In the United States alone, there are approximately 2.7 million infected individuals, with 150,000 acute cases occurring annually, resulting in HCV infection as the ninth leading cause of death.

Intravenous drug abuse has been indicated as one important risk factor for transmission of HCV. However, different epidemiological studies have revealed that for up to 20 to 40% of patients chronically infected with HCV, no known risk factors have been identified.

The disease associated with HCV is, in most cases, benign. Nevertheless, persistent infection can lead to liver cirrhosis and hepatocellular carcinoma. HCV disease can be manifested as acute viral hepatitis which is usually clinically mild, but may develop into a severe or fulminant hepatitis. Chronic HCV hepatitis is believed to occur more frequently than with hepatitis B virus, especially following posttransfusional acute hepatitis C disease.

Treatment of HCV infection has primarily been with alpha-interferon. In some instances liver transplantation has been performed for end-stage hepatic deficiency, but invariably the transplanted liver also becomes infected with HCV and ultimately fails.

Virally encoded gene products have been thought to be effective targets for drug development because they are unique to infected cells. However, despite the potential specificity of drugs targeting viral gene products, they have the disadvantage of rapidly becoming ineffective due to the ability of the virus to mutate and become drug resistant. This drug resistant phenomenon has been observed with both DNA and RNA virus. Moreover, similar phenomenon have been observed with other infectious agents such as paracytes which change coat proteins in response to specific targeting agents or host immune responses. In contrast, cellular genes that are essential for viral replication or expression are not rapidly mutated and therefore less susceptible to developing resistance. The availability of such cellular genes would be valuable as targets for development of new therapeutics and methods for treatment of a variety of viral and other infectious diseases.

Thus, there exists a need for the rapid and efficient identification of cellular genes involved in the propagation or pathogenesis of infectious agents. The present invention satisfies this need and provides related advantages as well.

SUMMARY OF THE INVENTION

The invention provides a substantially pure nucelic acid having a nucleotide greater than about 80% indentical to SEQ ID NO:1, or a unique fragment thereof. Also provided is a substantially pure polypeptide having an amino acid sequence greater than about 91% identical to SEQ ID NO:2, or functional fragment thereof. A substantially pure TST nucleic acid is further provided The TST nucleic acids consist of a fragment of SEQ ID NO:1 having substantially the nucleotide sequence $N_5$-GUC-$_8$ $N_5$-GUA-$N_5$ (SEQ ID NOS:3 and 4, respectively). The TST nucleic acids can be between 8–12 nucleotides at positions $N_5$ and $N_8$ are identical to a fragment of SEQ ID NO:1. Additionally provided is a TST nucleic acid having a sequence selected from the group consisting of 5'-UAGUNGUCAAAGUUAG-3', 3'-CGCANGUCAAUAAUUA-3', 5'-CUGANGUCUAGAUCGC-3', 3'-AAGCNGUCUUUGGUCU-3', 5'-CGGUNGUCCUGGCUGU-3', 3'-CGUANGUCGCGUUUAA-3', 5'-UUCGNGUCAGCCAAUA-3', 3'-GCAGNGUCGAGGCUGA-3', 5'-GCANGUCUGCCAGCU-3', 3'-AAGUNGUCAUUAACAA-3', 5'-AGCUNGUCAAUAAGAA-3', 3'-UUCCNGUCUUAAGCGA-3', 5'-AGAANGUCUUGACGAA-3', 3'-GUCUNGUCACGUGUUA-3', 5'-GGGANGUCCCUCGGCU3', 3'-CGAGNGUCGUUGACAG-3', 5'-UCCANGUCAUAUGAAU-3', 3'-GAUGNGUCCGCGCAAG-3', 5'-CUGCNGUCAUGCGGCU-3', (SEQ ID NOS:25–43) or a complementary sequence thereof. A method of identifying a compound that modulates the activity of a cellular regulator is further provided. The method consists of contacting a sample containing a cellular regulator and a nucleic acid element acted on by a cellular regulator with a test compound under conditions that allow replication or expression of the nucleic acid element or a gene operatively linked to the nucleic acid element, and measuring the amount of replication or expression of the nucleic acid element or gene, an increase or decrease in the amount of replicatin of expression in the presence of the test compound compared to the absence of the test compound indicates that the compound has cellular regulator modulatory activity. A method of treating a HCV infection is also provided.

BRIEF DESCRIPTION OF THE DRAWINGS

FIG. 5A shows the nucleotide and amino acid sequence of human eIF2Bγ (SEQ ID NOS:1 and 2, respectively). FIG. 5B shows an amino acid alignment of human and rat eIF2Bγ (SEQ ID NO:2 and SEQ ID NO:140, respectively).

DETAILED DESCRIPTION OF THE INVENTION

Figure 1:
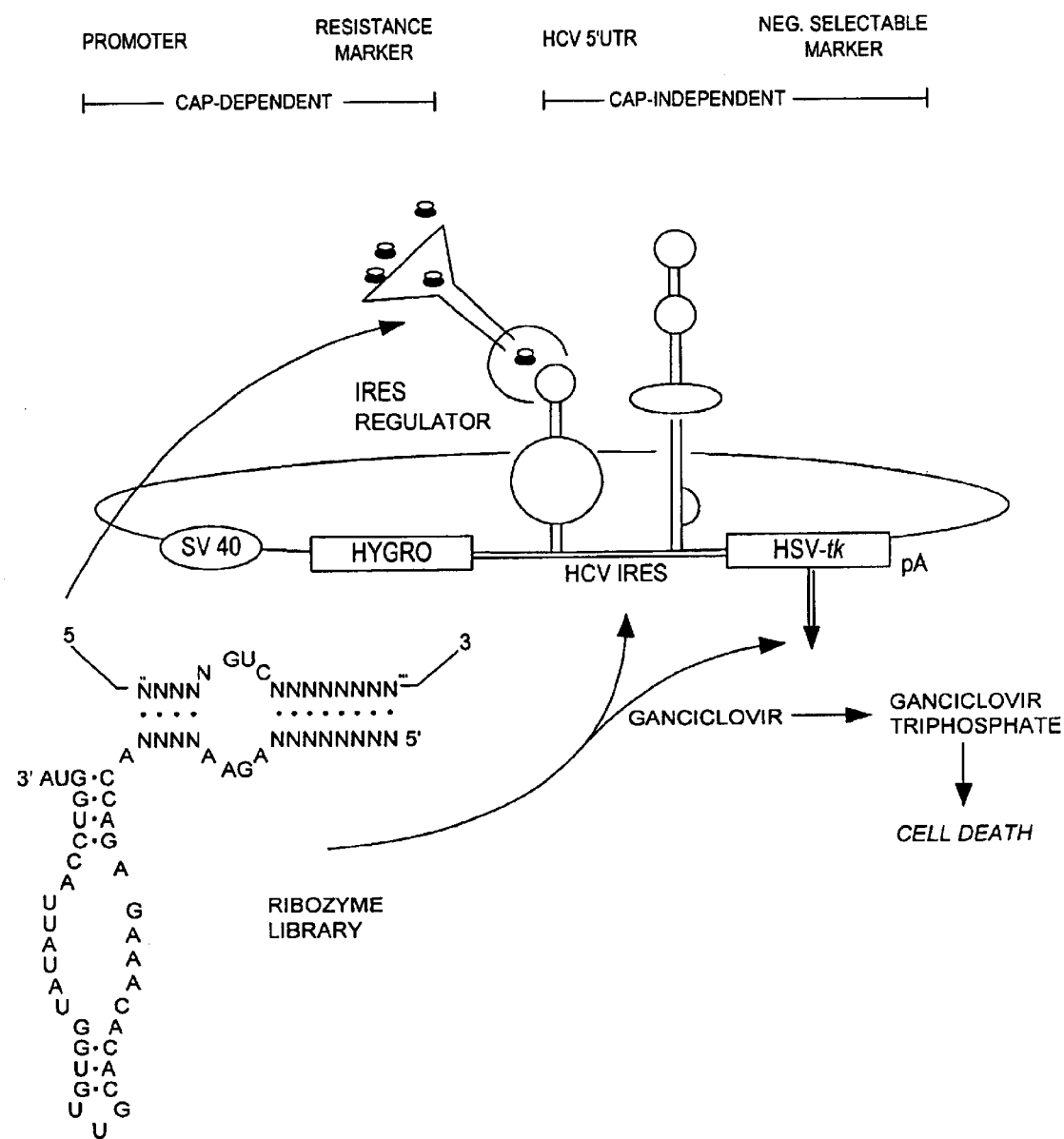
FIG. 1 shows a schematic representation of the vector construct and application of a randomized hairpin ribozyme library (SEQ ID NOS:3 and 141) for the discovery of HCV IRES regulator molecules.

The invention is directed to methods of identifying genes required for pathogenesis of infectious diseases and to the identified genes and gene products as therapeutic targets for the treatment of infectious diseases. The methods are directed to the identification of genes encoding cellular regulators of infectious agents such as Hepatitis C virus (HCV), for example. Genes encoding cellular regulators are sought for identification and as therapeutic targets because they are less susceptible to genetic adaptations, such as mutation to drug resistance, because cellular regulators are also required in host cell function.

In one embodiment, cellular regulators for HCV have been identified. HCV contains a nucleic acid sequence element present in its RNA that is recognized by cellular translation machinery and is essential for HCV polypeptide expression. The element, termed internal ribosome entry site (IRES), allows for entry of ribosomes and translation initiation at an internal sequences within an RNA. This translation pathway is distinct from the majority of cellular mRNA which requires the presence of a 5' cap structure for ribosome binding and subsequent translation initiation. A total of eighteen (18) cellular sequences have been identified which correspond to cellular regulators that function in HCV replication or expression. Two of the cellular regulators correspond to polypeptide subunits of the translation machinery and two of the cellular regulators correspond to a cellular proteasome complex. Inhibiting expression of any of these cellular regulators results in inhibition of IRES-mediated translation of RNA.

As used herein, the term "substantially pure" when used in reference to a nucleic acid or polypeptide of the invention is intended to mean a molecule that is in a form that is relatively free from cellular components such as lipids, polypeptides, nucleic acids or other cellular material that it is associated with in its natural state.

As used herein, the term "nucleic acid" is intended to mean a single- or double-stranded DNA or RNA molecule. For example, a nucleotide designated as "T" also is equivalent to a "U" nucleotide in a recited sequence. A nucleic acid molecule of the invention can be of linear, circular or branched configuration, and can represent either the sense or antisense strand, or both, of a native nucleic acid molecule. A reference to a nucleotide sequence of a nucleic acid molecule also includes reference to its unrecited complementary strand. The term also is intended to include nucleic acid molecules of both synthetic and natural origin. A nucleic acid molecule of natural origin can be derived from any animal, such as a human, non-human primate, mouse, rat, rabbit, bovine, porcine, ovine, canine, feline, or amphibian, or from a lower eukaryote, such as Drosophila, C. elegans or yeast. A synthetic nucleic acid includes, for example, chemical and enzymatic synthesis. The term "nucleic acid" is similarly intended to include analogues of natural nucleotides which have similar binding properties as the referenced nucleic acid and which can be utilized in a manner similar to naturally occurring nucleotides and nucleosides.

As used herein, the term "fragment" when used in reference to a nucleic acid is intended to mean a portion or segment of the nucleic acid molecule having the ability to selectively hybridize or bind to the subject nucleic acid, or its complement. The term "selectively hybridize" as used herein, refers to the ability of a nucleic acid or fragment to bind the subject nucleic acid molecule without substantial cross-reactivity with a molecule that is not the subject nucleic acid molecule.

A fragment of a nucleic acid molecule of the invention includes at least about 8–12 nucleotides of the subject nucleic acid. For example, the ribozyme sequence tag (RST) sequences and their corresponding target sequence tags (TST) sequences described herein contain about 8 nucleotides in helix 1 and about 4 nucleotides in helix 2, where about 4 of these nucleotides can lack sequence complementarity to the TST nucleic acid and still exhibit selective hybridization. Therefore, a fragment having the ability to selectively hybridize can contain about 8, 9, 10, 11 or 12 nucleotides of the subject nucleic acid. A fragment can also contain a greater number of nucleotides corresponding to the subject nucleic acid, or complement thereof, including for example, about 13, 14 or 15 nucleotides as well as at least 16, 17, 18, 19 or 20 nucleotides so long as it maintains the ability to selectively hybridize to the subject nucleic acid. Additionally, a fragment can be longer, including at least about 25, 30, 40, 50, 100, 300 or 500 or more nucleotides, and can include up to the full length of the reference nucleic acid molecule minus one nucleotide. Fragments of such lengths are able to selectively hybridize with the subject nucleic acid molecule in a variety of detection formats described herein and known to those skilled in the art. Fragments of the invention expressly exclude known EST sequences available to the public within EST databases as of the date of filing this application.

Therefore, a fragment of a nucleic acid molecule of the invention can be used, for example, as a RST to target a ribozyme to a nucleic acid of the invention; as a PCR primer to selectively amplify a nucleic acid molecule of the invention; as a selective primer for 5' or 3' RACE to determine or identify 5' or 3' sequence of a nucleic acid molecule identified in methods of the invention; as a selective probe to identify or isolate a nucleic acid molecule of the invention on a Northern or Southern blot, or from a genomic or cDNA library; or as a selective inhibitor of HCV replication or expression in a cell infected with HCV.

The term "unique" when used in reference to a specific nucleic acid fragment is intended to mean a fragment of the subject nucleic acid that contains at least one nucleotide at a particular position that is characteristic, distinct or novel when compared to a different nucleotide sequence, or a related nucleotide sequence at the same or analogous position. In reference to a particular sequence, for example, the human eIF2Bγ nucleotide sequence differs from the rat sequence at about 42 codon positions or about 126 nucleotides within the coding region. Therefore, for each of these codons positions, there is at least one nucleotide which differs from the rat sequence and is therefore characteristic of the human eIF2Bγ nucleotide sequence. An eIF2Bγ nucleic acid fragment containing one such characteristic nucleotide is a unique fragment.

As used herein, the term "substantially the same" when used in reference to a nucleotide sequence is intended to mean that a nucleic acid molecule that retains its ability to selectively hybridize to the reference nucleic acid. Therefore, a nucleic acid molecule having substantially the same sequence compared to a reference nucleic acid can include, for example, one or more additions, deletions or substitutions with respect to the reference sequence so long as it can selectively bind to that sequence. Included within this definition are encoding nucleic acids that have degenerate codon sequences at one or more positions and therefore differ in nucleotide sequence compared to the reference nucleic acid but substantially maintain the referenced encoded amino acid sequence.

As used herein the term "substantially the same" when used in reference to a polypeptide of the invention is intended to mean an amino acid sequence that contains minor modifications with respect to the reference amino acid sequence, so long as the polypeptide retains one or more of the functional activities exhibited by the polypeptide as a whole. A polypeptide that has substantially the same amino acid sequence as a reference human amino acid sequence can be, for example, a homologous polypeptide from a vertebrate species, such as a non-human primate, mouse, rat, rabbit, bovine, porcine, ovine, canine, feline, or amphibian, or from a lower eukaryote, such as Drosophila, *C. elegans* or yeast.

A polypeptide that has substantially the same amino acid sequence as a reference sequence can also have one or more deliberately introduced modifications, such as additions, deletions or substitutions of natural or non-natural amino acids, with respect to the reference sequence. Those skilled in the art can determine appropriate modifications that, for example, serve to increase the stability, bioavailability, bioactiviy or immungenicity of the polypeptide, or facilitate its purification, without altering the desired functional acitivity. For example, introduction of a D-amino acid or an amino acid analog, or deletion of a lysine residue, can stabilize a polypeptide and reduce degradation. Likewise, addition of tag sequeces, such as epitope or histidine tags, or sorting sequences, can facilitate purification of the recombinant polypeptide. Depending on the modification and the source of the polypeptide, the modification can be introduced into the polypeptide, or into the encoding nucleic acid sequence.

Computer programs known in the art, for example, DNASTAR software, can be used to determine which amino acid residues can be modified as indicated above without abolishing the desired functional activity. Additionally, guidance in modifying amino acid sequences while retaining functional activity is provided by aligning homologous cellular regulator polypeptides from various species. Those skilled in the art understand that evolutionarily conserved amino acid residues and domains are more likely to play a role in the biological activity than less well-conserved residues and domains.

In general, an amino acid sequence that is substantially the same as a reference amino acid sequence will have greater than about 70% identity, preferably greater than about 85% identity, more preferably greater than about 91% identity, including greater than about 94% identity with the reference sequence. The amino acid sequences which align across two sequences, and the presence of gaps and non-homologous regions in the alignment, can be determined by those skilled in the art based, for example, on a BLAST 2 or Clustal V or similar computer alignment. A computer alignment can, if desired, be optimized visually by those skilled in the art. The percent identity of two sequences is determined as the percentage of the total amino acids that align in such an alignment which are identical. Those skilled in the art understand that two amino acid molecules with a given percentage identity over the entire sequence or over a substantial portion or portions thereof, are more likely to exhibit similar functional activities than two molecules with the same percentage identity over a shorter portion of the sequence.

As used herein, the term "functional fragment" when used in reference to a polypeptide of the invention is intended to refer to a portion, segment or fragment of the polypeptide which retains at least one of the activities of the full length polypeptide. For example, a functional fragment of eIF2Bγ can be a portion of eIF2Bγ that maintains its ability to bind with one or more other subunits of eIF2B or a portion of eIF2Bγ that maintains its ability to facilitate GDP-GTP exchange with eIF2.

As used herein, the term "ribozyme sequence tag" or "RST" is intended to mean the complementary sequence of the target RNA selectively recognized or selectively recognized and cleaved by the target recognition sequence of a ribozyme. For example, the target RNA selectively recognized are the complements to the helix 1 and helix 2 regions described below. These complementary regions are separated by an AGAA sequence in the RST. Therefore, the structure of an RST can be 5'-$N_8$AGAA-$N_4$-3' (SEQ ID NO:5) where $N_8$ and $N_4$ represent, the complementary sequences of the target RNA recognized by the helix 1 and helix 2 ribozyme regions, respectively. Therefore, a target sequence tag nucleic acid or "TST" as used herein, is a nucleic acid having a nucleotide sequence that is complementary to and capable of selectively hybridizing to an RST. For example, the TST regions capable of selectively hybridizing to the RST will be substantially the complement of the helix 1 and helix 2 RST region sequences. These selectively hybridizing regions are separated by, for example, an GUC which is capable of being cleaved by a hairpin ribozyme and therefore will have the structure 5'-$N_5$-GUC-$N_8$-3' (SEQ ID NO:3) where the first four nucleotides of $N_5$ and $N_8$ represent the complementary sequence of the helix 2 and helix 1 ribozyme regions, respectively.

Figure 2:
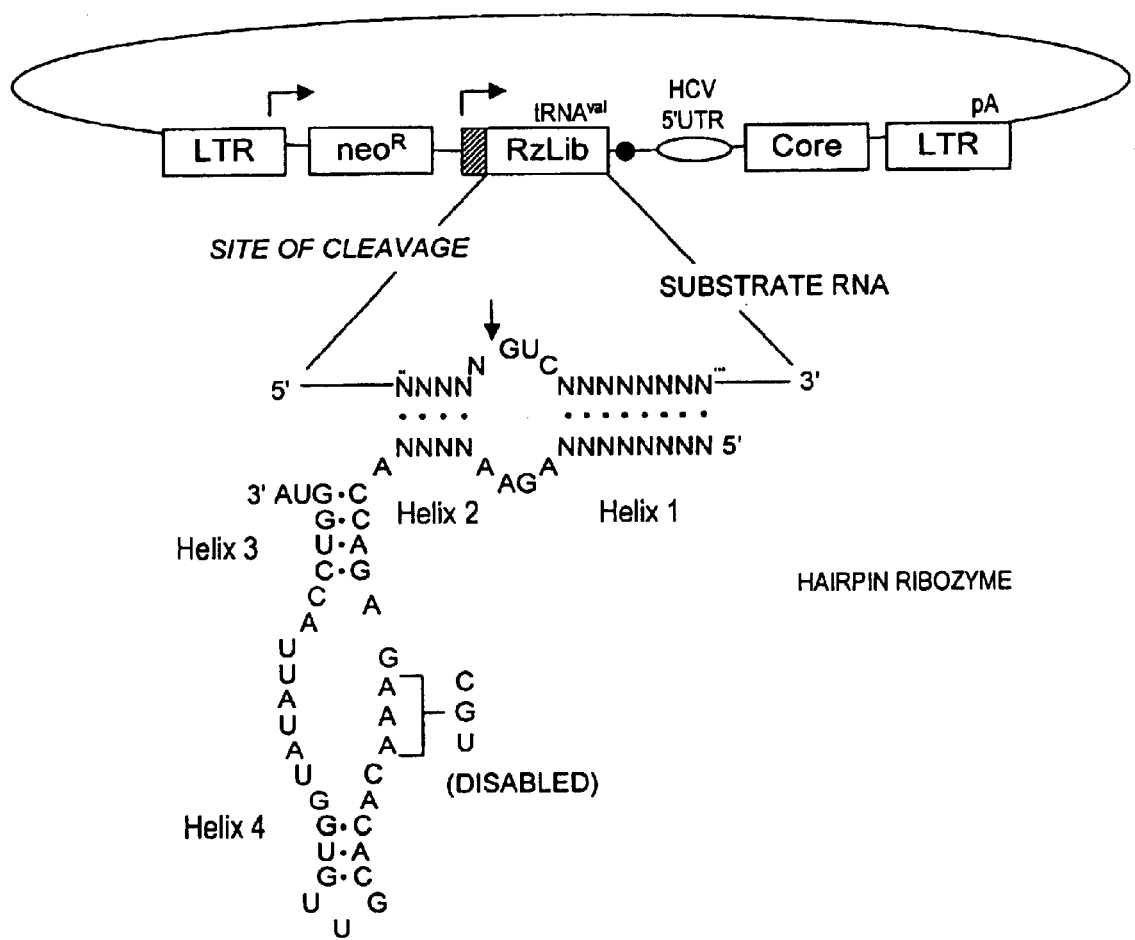
FIG. 2 shows a schematic representation of a hairpin ribozyme library (SEQ ID NOS:3, 141 and 142).

As used herein, the term "ribozyme" or "ribozyme RNA molecule" is intended to mean a catalytic RNA that cleaves RNA. Ribozymes include both hairpin and hammerhead classes which differ in mechanism for hybridization. The term "hairpin ribozyme" is intended to refer to an RNA molecule having the general nucleic acid sequence and two-dimensional configuration of the molecule shown in FIGS. 1 and 2, and which is capable of selectively hybridizing, or of both selectively hybridizing and cleaving, a target RNA. The term is also intended to include both hairpin ribozyme RNA molecules as well as single- and double-stranded DNA molecules that, when expressed, form hairpin ribozyme RNA molecules. Generally, a hairpin ribozyme will have from about 50 to 54 nucleotides, and forms two helical domains (Helix 3 and Helix 4) and 3 loops (Loops 2, 3 and 4). Two additional helices, Helix 1 and Helix 2, form between the ribozyme and its RNA target or substrate (FIG. 2). A hairpin ribozyme binds a target RNA by forming Watson-Crick base pairs between the substrate and Helix 1 and Helix 2 sequences, as shown by dots in FIGS. 1 and 2, where "N" is any nucleotide. The length of Helix 2 is usually about 4 nucleotides, and the length of Helix 1 can vary from about 6–10 nucleotides or more. A hairpin ribozyme can have catalytic activity, and thus cleave the target RNA at the indicated cleavage site in FIG. 2. The catalytic activity of the hairpin ribozyme also can be disabled by, for example, altering the AAA sequence in Loop 2 to CGU. Those skilled in the art can determine which modifications to the overall hairpin ribozyme structure can be made and still maintain the target binding, or both target binding and catalytic activity, of a hairpin ribozyme of the invention.

As used herein, the term "library" or "ribozyme library" is intended to mean a collection or population of different species of ribozyme RNA molecules. Within a population, any of the ribozyme species can be uniquely represented or redundant. Therefore, the term "randomized" or "random" when used in reference to a ribozyme library is intended to refer to a population of ribozymes that have differing nucleotide sequences in their target recognition sequence. The differing nucleotide sequences can be purposefully introduced, such as by degenerate, partially degenerate or varigated oligonucleotide synthesis, or other methods well known to those skilled in the art. Alternatively, the differing nucleotide sequences can be introduced by a variety of mutagenesis methods, including for example, chemical and enzymatic methods, known in the art. A random ribozyme library also can be assembled, for example, from combining a collection of different ribozyme species into a single population. The synthesis and construction of random ribozyme libraries is described further below in the Examples and is the subject matter of U.S. applications 60/037,352 and 60/093,828, both of which are explicitly incorporated herein by reference.

As used herein, the term "target recognition sequence" when used in reference to a ribozyme is intended to mean the substrate binding site of a ribozyme, which corresponds to an RST RNA nucleotide sequence or which corresponds to the complement of an TST nucleic acid nucleotide sequence. For the specific example of a hairpin ribozyme, the target recognition sequence corresponds to the nucleotide sequences of the helix 1 or helix 2 domain or both (See FIG. 2). The target recognition sequences of helix 1 and 2 can be separated by catalytic nucleotides, which in,the specific example of a hairpin ribozyme correspond to the nucleotides AGAA.

As used herein, the term "cellular regulator" when used in reference to virus replication or expression, is intended to mean a gene product, including structural or functional RNA gene products, that are encoded by an endogenous gene of an infected or uninfected cell. Endogenous genes can include, for example, genes originating from the species of the infected cell type as well as heterologous genes that become incorporated into the cell's genome so long as it is not derived from the genome of the infectious agent. To be a cellular regulator, the cellular gene product must also function in the replication or expression of the virus. It is not necessary that the cellular regulator is essential for virus replication or expression, but instead, that the cellular regulator is functionally involved in virus replication or expression.

As used herein, the term "negative selection marker" is intended to mean a gene product that is, or can be made to be cytotoxic or cytostatic to cells. Specific examples include thymidine kinase (tk), cytosine deaminase (CD) and diphtheria toxin (DT). For example, in the presence of nucleoside analogues, the expression of tk and CD is toxic to cells. The cognate compound used in negative selection for the above specific examples include ganciclovir or FIAU for tk and 5-fluorocytosine for cytosine deaminase. Diphtheria toxin is itself toxic because it inhibits protein synthesis and therefore is a non-conditional marker gene. However, diphtheria toxin can be made conditional by liking it to an inducible promoter or other regulatory element, for example.

As used herein, the term "treating" when used in reference to an HCV infection is intended to mean a reduction in severity, or prevention of an infectious disease. Therefore, "treating a HCV infection" as used herein, is intended to mean a reduction in severity, regression, or prevention of a HCV infection. Reduction in severity includes, for example, an arrest or a decrease in clinical symptoms, physiological indicators or biochemical markers. Prevention of the infection includes, for example, precluding the occurrence of the infection, such as in prophylactic uses to individuals susceptible to or suspected of exposure to HCV, or reversing an infected individual to their preinfectious state of health.

The invention provides a substantially pure nucleic acid comprising a nucleotide sequence greater than about 79% identical to SEQ ID NO:1, or a unique fragment thereof. Also provided is a substantially pure polypeptide comprising an amino acid sequence greater than about 91% identical to SEQ ID NO:2, or functional fragment thereof.

The nucleic acid shown as SEQ ID NO:1 has been found to encode a cellular regulator of HCV which functions in IRES-mediated translation of RNA. As such, it is useful as a target for treating or reducing the severity of HCV or other infectious agents which utilize IRES elements for replication or expression. Inhibition of the expression or activity of this cellular regulator results in a concomitant decrease in the infecting agent's polypeptide translation and therefore propagation as pathological agent.

SEQ ID NO:1 corresponds to the expressed message of the human gene encoding translation initiation factor 2B gamma subunit (eIF2Bγ). SEQ ID NO:1 is about 1602 nucleotides in length and has 5' and 3' non-coding regions of 102 and 112 nucleotides, respectively. The resultant coding region is 1359 nucleotides in length, coding for a polypeptide of 452 amino acids (FIG. 5A). SEQ ID NO:1 has a nucleotide sequence of about 88% identical to the rat sequence within the coding region where no other species of eIF2Bγ have yet to be identified.

Modifications of SEQ ID NO:1 which do not substantially affect the activity of the encoded cellular regulator and which maintain nucleotide sequence identity greater than about 80% are included as nucleic acids of the invention. These nucleic acids having minor modifications can similarly be used for the development of therapeutic compounds which inhibit the expression or activity of human eIF2Bγ cellular regulator. Such modifications include, for example, changes in the nucleotide sequence which do not alter the encoded amino acid sequence as well as changes in the nucleotide sequence with result in conservative amino acid substitutions or minor alterations which do not substantially affect the activity of eIF2Bγ. Those skilled in the art will known or can determine what changes within greater than about 80% compared to SEQ ID NO:1 can be made without substantially affecting the activity of eIF2Bγ as a cellular regulator of HCV replication or expression.

Unique fragments of SEQ ID NO:1 are also provided. The fragments are useful in a variety of procedures, including for example, as probes for determining the effectiveness of therapeutic agents which target expression of eIF2Bγ as a cellular regulator of HCV replication or expression, or other IRES-dependent infectious agent. Unique fragments also can be used to encode functional fragments of eIF2Bγ as therapeutic targets for anti-HCV compounds in the screening methods of the invention. The unique fragments of SEQ ID NO:1 are applicable in a variety of other methods and procedures known to those skilled in the art.

Unique fragments of SEQ ID NO:1 correspond to fragments or portions of SEQ ID NO:1 that are of sufficient length to distinguish the fragment as an eIF2Bγ encoding nucleic acid and that contain at least one nucleotide characteristic of SEQ ID NO:1. Such a characteristic nucleotide, or nucleotides, within a specific fragment of SEQ ID NO:1 distinguish that fragment from other related nucleotide sequences. For example, fragments of the non-coding region of SEQ ID NO:1 are generally unique when compared to even related nucleotide sequences such as the rat sequence, for example, because there is little evolutionary pressure to conserve non-coding domains. Nucleic acid sequences as small as between about 12–15 nucleotides are statistically unique sequences within the human genome. However, nucleic acids as small as between about 8–12 nucleotides can be unique. Therefore, non-coding region fragments of SEQ ID NO:1 of about 8–9, preferably about 10–11, and more preferably about 12 or 15 nucleotides or more in length can be nucleotide sequences corresponding to unique fragments of SEQ ID NO:1 of the invention.

Additionally, unique nucleotide sequences arise in the coding region of SEQ ID NO:1 as well. Those skilled in the art will know or can determine which nucleotide positions are unique to either a non-coding region or a coding region fragment of SEQ ID NO:1 given the teachings described herein or by alignment using methods well known to those skilled in the art of SEQ ID NO:1 with other sequences to be distinguished. Moreover, for ease of reference to distinguishing nucleotides within codon positions, FIG. 5B shows an amino acid sequence alignment of the polypeptide encoded by SEQ ID NO:1 with a rat eIF2Bγ amino acid sequence. The alignment shows that there are about 43 codon differences between these two sequences, indicating at least about 42 or more unique nucleotides in SEQ ID NO:1 compared to the encoding rat nucleotide sequence. Comparison of SEQ ID NO:1 with the nucleotide sequence of rat eIF2Bγ will reveal that within these 43 codons there are 52 nucleotide differences. Inclusion of any or all of these distinguishing nucleotide differences within a fragment of SEQ ID NO:1 confers uniqueness onto the fragment.

A substantially pure nucleic acid molecule having a nucleotide sequence greater than about 80% identical to SEQ ID NO:1, or a unique fragment thereof, will be of sufficient length and identity to SEQ ID NO:1 to selectively hybridize to it under at least moderately stringent hybridization conditions. For example, it can be determined that a substantially pure nucleic acid molecule contains a nucleotide sequence greater than about 80% as SEQ ID NO:1, or a unique fragment thereof, by determining its ability to hybridize in a filter hybridization assay to a molecule having the sequence of SEQ ID NO:1, but not to other unrelated nucleic acid molecules, under conditions equivalent to hybridization in 50% formamide, 5× Denhart's solution, 5×SSPE, 0.2% SDS at 42° C., followed by washing in 0.2×SSPE, 0.2% SDS, at 65° C. Suitable alternative buffers and hybridization conditions that provide for moderately stringent hybridization conditions in particular assay formats are known or can be determined by those skilled in the art (see, for example, Sambrook et al., *Molecular Cloning. A Laboratory Manual*, Cold Spring Harbor Laboratory Press, 1989).

The nucleic acid shown as SEQ ID NO:1 encodes a polypeptide that is 91% identical to rat eIF2Bγ. The amino acid sequence corresponding to the eIF2Bγ cellular regulator is shown in SEQ ID NO:2. As with the nucleotide sequence described above, modifications of SEQ ID NO:2 which do not substantially affect the activity of the cellular regulator and which maintain amino acid sequence identity greater than about 91% are included as polypeptides of the invention. These polypeptides having minor modifications can similarly be used for the development of therapeutic compounds which inhibit the activity of human eIF2Bγ cellular regulator. Such modifications include, for example, changes in the amino acid sequence which do not substantially alter the structure or function of a domain within the polypeptide as well as changes in the amino acid sequence with result in conservative substitutions or minor alterations which do not substantially affect the activity of eIF2Bγ. Those skilled in the art will known or can determine what changes within greater than about 9% compared to SEQ ID NO:2 can be made without substantially affecting the activity of eIF2Bγ as a cellular regulator of HCV replication or expression.

Functional fragments of SEQ ID NO:2 are also provided. The cellular regulator eIF2Bγ is a subunit of a GDP-GTP exchange protein necessary for recharging the cellular regulator eIF2 translation initiation factor with GTP following one cycle of peptide bond formation. Therefore, a specific example of a functional fragment is the domain which binds one or more subunits within the eIF2B complex or the domain which directly or indirectly participates conferring GTP binding specificity onto the eIF2B complex. Other functional fragments of eIF2Bγ also exist and are known, or can be determined by those skilled in the art.

The invention also provides a substantially pure TST nucleic acid consisting of a fragment of SEQ ID NO:1 having substantially the nucleotide sequence 5'-$N_5$-GUC-$N_8$' or 5'-$N_5$-GUA-$N_8$-3' (SEQ ID NOS:3 and 4, respectively). The TST nucleic acid portion of the fragment can have between about 8–12 nucleotides, and preferably about 9–10 nucleotides at positions $N_5$ and $N_8$ that are identical to a fragment of SEQ ID NO:1. Therefore, depending on the length of the TST nucleic acid portion, a fragment of SEQ ID NO:1 as described above can be about 11–15 nucleotides or greater in length.

Hairpin ribozymes cleave RNA substrates 5' to the G nucleotide in either of the sequences 5'-$N_5$-GUC-$N_8$-3' or 5'-$N_5$-GUA-$N_8$-3' (SEQ ID NOS:3 and 4, respectively) Fragments of SEQ ID NO:1 having a corresponding RNA form that is recognized by the target recognition site of a hairpin ribozyme therefore include nucleic acids having the sequence 5'-$N_5$-GUC-$N_8$-3' or 5'-$N_5$-GUA-$N_8$-3' (SEQ ID NOS:3 and 4, respectively) where $N_5$ and $N_8$ are nucleotide sequences substantially the same as a sequence corresponding to SEQ ID NO:1. Such fragments correspond to the complement sequence of a ribozyme target recognition site or RST and are referred to herein as TST nucleic acids.

The TST nucleic acids can be of any desired length and can include additional sequences other than those corresponding to SEQ ID NO:1 and other moieties so long as they have the structure 5'-$N_5$-GUC-$N_8$-3' or 5'-$N_5$-GUA-$N_8$-3' (SEQ ID NOS:3 and 4, respectively) where $N_5$ and $N_8$ correspond substantially a nucleotide sequence of SEQ ID NO:1. Moreover, it is not necessary for all nucleotide residues within the $N_5$ and $N_8$ regions to be identical to the corresponding sequence within SEQ ID NO:1. Instead, all that is necessary is for such TST nucleic acids to selectively hybridize to a complementary RST. Therefore, less than all 13 nucleotides at positions $N_5$ and $N_8$ can be identical to a nucleotide sequence or fragment of SEQ ID NO:1. Generally, between about 8–12 or between about 9–10 nucleotides are sufficient for selective hybridization of an RST with a TST nucleic acid. Described further below in the Examples is a specific example of an RST present in a ribozyme that selectively hybridizes to SEQ ID NO:1.

Similarly, the TST nucleic acids can be used to design ribozymes that selectively hybridize and cleave a RNA corresponding to SEQ ID NO:1. A specific example of such a ribozyme is a hairpin ribozyme having a target recognition sequence complementary to a TST nucleic acid of SEQ ID NO:1 and having the nucleotide sequence 5'-$N_8$-AGAA-$N_4$-3' (SEQ ID NO:5). As with the TST nucleic acids described above, it is not necessary that all the sequences with position $N_8$ and N4 be identical in complement to SEQ ID NO:1 so long as the target recognition sequence can selectively hybridize to the RNA form of TST nucleic acid and cleave it as a substrate. Those skilled in the art will know or can determine given the teachings and descriptions herein what RST sequences are sufficient for selective hybridization as well as for cleavage of a target RNA substrate.

Therefore, the invention provides a ribozyme having a target recognition sequence capable of selectively hybridizing to a RNA corresponding to SEQ ID NO:1 and cleaving said RNA. The target recognition sequence of the ribozyme can consist of an RST complementary to a fragment of SEQ ID NO:1 and having substantially the nucleotide sequence 5'-$N_8$-AGAA-$N_4$-3' (SEQ ID NO:5). The target recognition sequence can further be between about 8–12 nucleotides, preferably about 9–10 nucleotides at positions $N_8$ and $N_4$ that are complementery to a fragment of SEQ ID NO:1.

The invention further provides a RST having one of the following nucleotide sequences:
5'-CUAACUUUAGAAACUA-3',
5'-UAAUUAUUAGAAUGCG-3',
5'-GCGAUCUAAGAAUCAG-3',
5'-AGACCAAAAGAAGCUU-3',
5'-ACAGCCAGAGAAACCG-3',
5'-UUAAACGCAGAAUACG-3',
5'-UAUUGGCUAGAACGAA-3',
5'-UCAGCCUCAGAACUGC-3',
5'-AGCUGGCAGAACUGC-3',
5-UUGUUAAUAGAAACUU-3',
5'-UUCUUAUUAGAAAGCU-3',
5'-UCGCUUAAAGAAGGAA-3',
5'-UUCGUCAAAGAAUUCU-3',
5'-UAACACGUAGAAAGAC-3',
5'-AGCCGAGGAGAAUCCC-3',
5'-CUGUCAACAGAACUCG-3',
5'-AUUCAUAUAGAAUGGA-3',
5'-CUUGCGCGAGAACAUC-3',
5'-AGCCGCAUAGAAGCAG-3' (SEQ ID NOS:6–24, respectively), or a complementary sequence thereof, as described further below. The complementary sequence at positions 9–12 (5'-AGAA-3') can be substituted by the non-complementary ribozyme cleavage sequence 5'-NGUC-3'.

As described herein, SEQ ID NOS:6–24 represent RST sequences of ribozyme binding sites selective for mRNAs whose cleavage resulted in loss of translation of an IRES-dependent RNA. Each of these sequences correspond to a nucleic acid encoding a cellular regulator of HCV replication or expression. As described previously with respect to TST nucleic acid fragments of the cellular regulator shown as SEQ ID NO:1, the 5' terminal $N_8$ positions and the 3' terminal $N_5$ positions are separated by the intervening trinucleotide sequence 5'-GUC-3' in the cellular regulator RNA and correspond to the complement of the RST sequence or the TST sequence. Also as described previously, at least about 8–12 nucleotides within positions $N_8$ and $N_5$ of a TST are sufficient for selective binding between a ribozyme and its celllular regular target RNA. Therefore, a cellular regulator nucleic acid molecule of the invention contains at least about 8–12 nucleotides corresponding to a RST sequence set forth as SEQ ID NOS:6–24, or its TST sequence complement corresponding to SEQ ID NOS:25–43, or about 11–15 nucleotides corresponding to a RST sequence set forth as SEQ ID NOS:6–24, or its TST sequence complement corresponding to SEQ ID NOS:25–43, and including the intervening trinucleotide 5'-GUC-3'.

Therefore, the invention also provides a TST nucleic acid having one of the following nucleotide sequences:
3'-UAGUNGUCAAAGUUAG-5',
5'-CGCANGUCAAUAAUUA-3',
3'-CUGANGUCUAGAUCGC-5',
5'-AAGCNGUCUUUGGUCU-3',
3'-CGGUNGUCCUGGCUGU-5',
5'-CGUANGUCGCGUUUAA-3',
3'-UUCGNGUCAGCCAAUA-5',
5'-GCAGNGUCGAGGCUGA-3',
3'-GCANGUCUGCCAGCU-5',
5'-AAGUNGUCAUUAACAA-3',
3'-AGCUNGUCAAUAAGAA-5',
5'-UUCCNGUCUUAAGCGA-3',
3'-AGAANGUCUUGACGAA-5',
5'-GUCUNGUCACGUGUUA-3',
3'-GGGANGUCCCUCGGCU-5',
5'-CGAGNGUCGUUGACAG-3',
3'-UCCANGUCAUAUGAAU-5',
5'-GAUGNGUCCGCGCAAG-3',
3'-CUGCNGUCAUGCGGCU-5', (SEQ ID NOS:25–43, respectively), or a complementary sequence thereof.

For simplicity of the description, the cellular regulator nucleic acids of the invention will be described with reference to its TST nucleic acid sequence and specifically with reference to a cellular regulator nucleic acid containing at least about 8–12 nucleotides corresponding to a TST nucleic acid sequence of SEQ ID NOS:25–43. However, it is to be understood that reference to a cellular regulator TST nucleotide sequence also specifically includes reference to the complementary sequence of the RST nucleic acid molecule. Therefore, it is also to be understood that reference to a cellular regulator containing at least about 8–12 nucleotides corresponding to a TST sequence of SEQ ID NOS:25–43 also includes reference to a cellular regulator nucleic acid containing at least about 11–15 nucleotides corresponding to a TST sequence set forth as SEQ ID NOS:25–43, which includes the intervening trinucleotide 5'-GUC-3' between the 5' terminal $N_5$ positions and the 3' terminal Ns positions and as described previously with respect to the cellular regulator shown as SEQ ID NO: 1 and its TST fragments. Therefore, the invention also provides substantially pure TST nucleic acids having the structure 5'-$N_5$-GUC-$N_8$-3' (SEQ ID NO:3) or 5'-$N_5$-GUA-$N_8$-3' (SEQ ID NO:4) and substantially the nucleotide sequences shown as SEQ ID NOS:25–43.

A cellular regulator nucleic acid molecule containing at least about 8–12 nucleotides corresponding to a TST nucleic acid sequence set forth as SEQ ID NOS:25–43, or about 11–15 nucleotides corresponding to a TST nucleic acid sequence set forth as SEQ ID NOS;25–43, and including the interventing trinucleotide 5'-GUC-3', or a functional fragment thereof, does not have the exact endpoints of nucleotide sequences deposited and available in public databases as of the date of filing the subject application. Such databases include, for example, the non-redundant GenBank database and NCBI dbest EST database. EST sequences for the above-described cellular regulators include GenBank accession numbers: AA703831, AI800599.1, AI632282.1, W58368, W58049, AI660531.1, AI798535.1, AI143649, AI040925, AA102365, AA991764, AA587233, AA580025, AI637675.1, W22190, AI937500.1, T78051, R38705, T90276, T82858, AA507077, Z41323, Z45650, AA649500, T75394, AI700227.1, F01614, AI359536, AA582198, F00408, AA322492, Z24924, F31617.1, AA102364, AA905387, C21034, F05355, AA933569, F34596.1, AI970443.1, AA308943, AA323715, R61886, AA130818, AA311999, AA076401, and AA703831.

A cellular regulator nucleic acid molecule of the invention containing at least about 8–12 nucleotides corresponding to a TST sequence set forth as SEQ ID NOS:25–43, can be advantageously used, for example, as therapeutic targets for the treatment of HCV infections, or to identify and isolate additional sequences corresponding to other regions of the cellular regulator nucleic acid molecules of the invention. When used for the latter purpose, the nucleic acid molecule can contain none, one, or many nucleotides at the 5' or 3' end, or both, of the TST sequences recited as SEQ ID NOS:25–43. These additional nucleotides can correspond to the native sequence of the cellular regulator nucleic acid molecule, or can be non-native sequences, or both. For example, non-native flanking sequences that correspond to a restriction endonuclease site or a tag, or which stabilize the nucleic acid containing at least about 8–12 nucleotides corresponding to a TST nucleic acid sequence set forth as SEQ ID NOS:25–43, in a hybridization assay, can be advantageous when the nucleic acid molecule is used as a probe or primer to identify or isolate longer cellular regulator nucleic acid molecules.

Native cellular regulator nucleotide sequences flanking the at least about 8–12 nucleotides corresponding to a TST sequence set forth as SEQ ID NOS:25–43, can be determined by methods known in the art, such as RT-PCR, 5' or 3' RACE, screening of cDNA or genomic libraries, and the like, using an oligonucleotide having at least about 8–12 nucleotides corresponding to the TST sequence of SEQ ID NOS:25–43 as a primer or robe, and sequencing the resultant product. The appropriate source of template RNA or DNA for amplification, extension or hybridization screening can be determined by those skilled in the art.

A specific example of a substantially pure cellular regulator nucleic acid molecule containing at least about 8–12 nucleotides of a TST corresponding to SEQ ID NOS:25–43 and flanking coding sequence is the cellular regulator nucleic acid molecule having the nucleotide sequence set forth as SEQ ID NO:1. The isolation of SEQ ID NO:1, based on knowledge of the RST sequence of SEQ ID NO:16, is described further below in the Examples. Moreover, SEQ ID NOS:6, 18 and 24, have similarly been used to identify the nucleic acids for eIF2γ and proteasome alpha subunit as cellular regulators of IRES-dependent translation. Therefore, such procedures can be used to identify and substantially purify longer nucleic acid molecules that contain at least about 8–12 nucleotides corresponding to a TST of SEQ ID NOS:25–43. Such molecules and their functional fragments can be used to produce cellular regulator polypeptides and specific antibodies, for example, by methods known in the art and described herein, for use in the diagnostic and therapeutic methods described herein and known in the art.

As described previously, a cellular regulator nucleic acid molecule, when functionally inactivated in a cell, results in the inhibition of IRES-dependent translation. Such inhibition results in the concomitant decrease in HCV, or other IRES-dependent infectious agent, replication or expression. Similar results can be observed by inactivation of the cellular regulator polypeptide by, for example, inhibiting its activity. The cellular regulator activity of a nucleic acid molecule containing at least about 8–12 nucleotides corresponding to a TST of SEQ ID NOS:25–43 and additional native nucleic acid sequences can be further demonstrated using various methods known in the art and described herein. For example, nucleic acid sequences flanking the SEQ ID NOS:25–43 sequences can be selectively targeted in a cell with ribozymes by the methods described herein. The effect on propagation of the infectious agent can be determined by the assays described below. If inactivation by ribozymal cleavage of a second sequence within the isolated nucleic acid molecule also results in a decreased propagation of the infectious agent, that nucleic acid molecule is a confirmed cellular regulator nucleic acid molecule.

Similarly, other types of methods can be used to corroborate the activity of a cellular regulator nucleic acid containing at least about 8–12 nucleotides of a TST corresponding to SEQ ID NO:25–43. For example, an antibody or other selective agent that binds a polypeptide encoded by the nucleic acid molecule can be introduced into the cell, and the effect of the antibody on infection, propagation or IRES-dependent translation of the agent determined. Similarly, an antisense nucleic acid that inhibits transcription or translation of the cellular regulator nucleic acid can be introduced into a cell, and the effect of the antisense nucleic acid on infection or propagation determined. Likewise, an altered form of a cellular regulator nucleic acid molecule, such as a dominant-negative mutant, can be expressed in a cell and its encoded polypeptide will compete with or mimic an endogenous cellular regulator molecule, and thus inhibit infection, propagation or IRES-dependent translation. Those skilled in the art can determine other appropriate assays to demonstrate that a substantially pure nucleic acid molecule containing at least about 8–12 nucleotides of any of SEQ ID NOS:25–43 have cellular regulator activity.

The TST sequences set forth as SEQ ID NOS:25–43, were identified from a random hairpin ribozyme library by assessing the ability of their corresponding RST to inhibit IRES-dependent translation (SEQ ID NOS:6–24). Therefore, the invention provides ribozymes containing the RST sequences set forth as SEQ ID NOS:6–24 as the ribozyme target recognition sequence. The hairpin ribozymes of the invention selectively bind to cellular regulator mRNA molecules complementary, in part, to these RST sequences.

A substantially pure hairpin ribozyme of the invention can be catalytic, so as to bind and cleave a cellular regulator nucleic acid messenger RNA. A catalytic hairpin ribozyme of the invention can therefore be used to selectively regulate the activity of a cellular regulator nucleic acid molecule of the invention. A substantially pure hairpin ribozyme of the invention can also be catalytically disabled, for example, by replacement of the Loop 2 AAA sequence indicated in FIG. 2 with a UGC sequence, so as to bind, but not cleave, a cellular regulator nucleic acid molecule of the invention. A non-catalytic hairpin ribozyme can be used, for example, as a control for the inhibition activity of non-disabled ribozymes.

Therefore, the invention also provides a ribozyme containing a target recognition sequence having any one of the following nucleotide sequences:
5'-CUAACUUUAGAAACUA-3',
5'-UAAUUAUUAGAAUGCG-3',
5'-GCGAUCUAAGAAUCAG-3',
5'-AGACCAAAAGAAGCUU-3',
5'-ACAGCCAGAGAAACCG-3',
5'-UUAAACGCAGAAUACG-3',
5'-UAUUGGCUAGAACGAA-3',
5'-UCAGCCUCAGAACUGC-3',
5'-AGCUGGCAGAACUGC-3',
5'-UUGUUAAUAGAAACUU-3',
5'-UUCUUAUUAGAAAGCU-3',
5'-UCGCUUAAAGAAGGAA-3',
5'-UUCGUCAAAGAAUUCU-3',
5'-UAACACGUAGAAAGAC-3',
5'-AGCCGAGGAGAAUCCC-3', 5'-CUGUCAACAGAACUCG-3',
5'-AUUCAUAUAGAAUGGA-3',
5'-CUUGCGCGAGAACAUC-3',
5'-AGCCGCAUAGAAGCAG-3' (SEQ ID NOS:6–24, respectively).

The nucleic acid molecules of the invention, including cellular regulator nucleic acid molecules and fragments, and hairpin ribozyme nucleic acid molecules, can be produced or isolated by methods known in the art. The method chosen will depend, for example, on the type of nucleic acid molecule one intends to isolate. Those skilled in the art, based on knowledge of the nucleotide sequences described herein, can readily isolate cellular regulator nucleic acid molecules as genomic DNA, or desired introns, exons or regulatory sequences therefrom; as full-length cDNA or desired fragments therefrom; or as full-length mRNA or desired fragments therefrom, by methods known in the art. Likewise, those skilled in the art can produce or isolate hairpin ribozymes selective for these sequences.

A useful method of isolating a cellular regulator nucleic acid molecule of the invention involves amplification of the nucleic acid molecule using the polymerase chain reaction (PCR), and purification of the resulting product by gel electrophoresis. For example, either PCR or reverse-transcription PCR (RT-PCR) can be used to produce a cellular regulator nucleic acid molecule having any desired nucleotide boundaries. Desired modifications to the nucleic acid sequence can also be introduced by choosing an appropriate primer with one or more additions, deletions or substitutions. Such nucleic acid molecules can be amplified exponentially starting from as little as a single gene or mRNA copy, from any cell, tissue or species of interest. An example of the isolation of a cellular regulator nucleic acid molecule using PCR is presented below in the Examples.

A further method of producing or isolating a cellular regulator nucleic acid molecule of the invention is by screening a library, such as a genomic library, cDNA library or expression library, with a detectable agent. Such libraries are commercially available or can be produced from any desired tissue, cell, or species of interest using methods known in the art. For example, a cDNA or genomic library can be screened by hybridization with a detectably labeled nucleic acid molecule having a nucleotide sequence disclosed herein. Additionally, an expression library can be screened with an antibody raised against a polypeptide corresponding to the coding sequence of a cellular regulator nucleic acid disclosed herein. The library clones containing cellular regulator nucleic acid molecules of the invention can be purified away from other clones by methods known in the art.

Furthermore, nucleic acid molecules of the invention can be produced by sythetic means. For example, a single strand of a nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as RST or hairpin ribozyme nucleic acid molecules, as well as hybridization probes and primers.

If it is desired to subclone, amplify or express a substantially pure nucleic acid molecule of the invention, the isolated nucleic acid molecule can be inserted into a commercially available cloning or expression vector using methods known in the art. Appropriate regulatory elements can be chosen, if desired, to provide for constitutive, inducible or cell type-specific expression in a host cell of choice, such as a bacterial, yeast, amphibian, insect or mammalian cell, including human cells. Those skilled in the art can determine an appropriate host and vector system for cloning a nucleic acid molecule of the invention or for expressing and purifying its encoded polypeptide.

Methods for introducing a cloning or expression vector into a host cell are well known in the art and include, for example, various methods of transfection such as the calcium phosphate, DEAE-dextran and lipofection methods, viral transduction, electroporation and microinjection. Host cells expressing cellular regulator nucleic acid molecules can be used, for example, as a source to isolate recombinantly expressed cellular regulator polypeptides, to identify and isolate molecules that regulate or interact with cellular regulator nucleic acids and polypeptides, or to screen for compounds that enhance or inhibit the activity of a cellular regulator molecule of the invention, as described further below.

The methods of isolating, cloning and expressing nucleic acid molecules of the invention described herein are routine in the art and are described in detail, for example, in Sambrook et al., *Molecular Cloning: A Laboratory Manual*, Cold Spring Harbor Laboratory, New York (1992) and in Ansubel et al., *Current Protocols in Molecular Biology*, John Wiley and Sons, Baltimore, Md. (1989).

Cellular regulator polypeptides and functional fragments of the invention can be isolated or prepared by methods known in the art, including biochemical, recombinant and synthetic methods. For example, a cellular regulator polypeptide can be purified by routine biochemical methods from a cell or tissue source that expresses abundant amounts of the corresponding transcript or polypeptide. Biochemical purification can include, for example, steps such as solubilization of the appropriate tissue or cells, isolation of desired subcellular fractions, size or affinity chromatography, electrophoresis, and immunoaffinity procedures. The methods and conditions for biochemical purification of a polypeptide of the invention can be chosen by those skilled in the art, and purification monitored, for example, by an ELISA assay or a functional assay.

A fragment having any desired boundaries and modifications to a cellular regulator amino acid sequences can also be produced by recombinant methods. Recombinant methods involve expressing a nucleic acid molecule encoding the desired polypeptide or fragment in a host cell or cell extract, and isolating the recombinant polypeptide or fragment, such as by routine biochemical purification methods described above. To facilitate identification and purification of the recombinant polypeptide, it can be desirable to insert or add, in-frame with the coding sequence, nucleic acid sequences that encode epitope tags, polyhistidine tags, glutathione-S-transferase (GST) domains, and similar affinity binding sequences, or sequences that direct expression of the polypeptide in the periplasm or direct secretion. Methods for producing and expressing recombinant polypeptides in vitro and in prokaryotic and eukaryotic host cells are well known in the art.

Functional fragments of a cellular regulator polypeptide can also be produced, for example, by enzymatic or chemical cleavage of the full-length polypeptide. Methods for enzymatic and chemical cleavage and for purification of the resultant peptide fragments are well known in the art (see, for example, Deutscher, *Methods in Enzymology*, Vol. 182, "Guide to Protein Purification," San Diego: Academic Press, Inc. (1990), which is incorporated herein by reference).

Furthermore, functional fragments of a cellular regulator polypeptide can be produced by chemical synthesis. If desired, such as to optimize their functional activity, stability or bioavailability, such molecules can be modified to include D-stereoisomers, non-naturally occurring amino acids, and amino acid analogs and mimetics. Examples of modified amino acids and their uses are presented in Sawyer, *Peptide Based Drug Design*, ACS, Washington (1995) and Gross and Meienhofer, *The Peptides: Analysis. Synthesis. Biology*, Academic Press, Inc., New York (1983), both of which are incorporated herein by reference.

A functional activity of an cellular regulator polypeptide or fragment of the invention can be its ability to alter, such as inhibit, IRES-dependent translation when expressed or introduced in a cell. To determine whether a given polypeptide or fragment has the ability to alter IRES-dependent translation; a polypeptide or fragment can be expressed in the cell by recombinant methods known in the art and the effect of the cellular regulator can be determined in vitro. Alternatively, expression of the cellular regulator can be inhibited in vivo, including cell culture or animal models and the replication or expression of the infectious agent can be determined. Similarly, expression of the cellular regulator can be inhibited in vivo, including cell culture or animal models and the expression of an IRES-dependent reporter marker determined. A decrease in the replication or expression of the infectious agent or in the expression of an IRES-dependent reporter marker indicates that the polypeptide or fragment is a cellular regulator of the invention.

The invention further provides a method of identifying a compound that inhibits the activity of a cellular regulator. The method consists of contacting a sample containing a cellular regulator and a nucleic acid element acted on by a cellular regulator with a test compound under conditions that allow replication or expression of the nucleic acid element or a gene operatively linked to the nucleic acid element, and measuring the amount of replication or expression of the nucleic acid element or the gene, a decrease in the amount of replication or expression in the presence of the test compound compared to the absence of the test compound indicates that the compound has cellular regulator inhibitory activity. The magnitude of the decrease in replication or expression activity will correlate with the cellular regulator inhibitory activity of the test compound.

Similarly, compounds that increase or enhance the activity of cellular regulator also can be identified. A test compound added to a sample containing a cellular regulator and a nucleic acid element acted on by a cellular regulator which increases the amount or rate of replication or expression of the nucleic acid or a gene operatively linked to the nucleic acid element compared to the absence of the test compound indicates that the compound increases the activity of the cellular regulator. Therefore, the invention provides a method of identifying compounds that modulate the activity of a cellular regulator.

A reaction system for identifying a compound that inhibits or increases cellular regulator activity can be prepared using essentially any sample, material or components thereof that contains a cellular regulator. A cellular regulator containing sample used for such methods can be, for example, in vitro transcription or translation systems using, for example, nucleic acid derived from the infectious agent or a hybrid construct linking the nucleic acid element acted on by a cellular regulator to a reporter gene. Alternatively, cellular nucleic acids and proteins can also be used since the cellular regulator also acts on nucleic acid elements of the host machinery. The cellular regulator containing sample can additionally be derived from cell extracts, cell fractions or, for example, in vivo systems such as cell culture or animal models which contain a nucleic acid element acted on by a cellular regulator. The replication levels of these nucleic acids, or the expression levels or activity of encoded products derived from the infectious agent or the reporter gene can be measured in the reaction system to determine the modulatory effect of the test compound on the cellular regulator. Such measurements can be determined using methods described herein as well as methods well known to those skilled in the art.

Briefly, the cellular regulator source is combined with a nucleic acid element or protein acted on by a cellular regulator as described above and incubated in the presence or absence of a test compound. The amount or rate of replication or expression from the nucleic acid in the presence of the test compound is compared with that in the absence of the test compound. Those test compounds which provide inhibition of replication or expression of at least about 50% are considered to be cellular regulator inhibitors, or antagonists, and further as potential therapeutic compounds for the treatment infectious diseases mediated by the donor agent of the nucleic acid element. Similarly, those compounds which increase the cleavage activity of about two-fold or more are considered to be compounds which increase the activity of a cellular regulator, or cellular regulator agonists. Such agonists can be used as therapeutics, for example, to shift the balance of cellular machinery use away from the replication or expression of the infectious agent. Compounds identified to modulate cellular regulator activity can, if desired, be subjected to further in vitro or in vivo studies to corroborate that they affect the activity of a cellular regulator toward the replication or expression of an infectious agent.

Suitable test compounds for the above-described assays can be any substance, molecule, compound, mixture of molecules or compounds, or any other composition which is suspected of being capable of inhibiting cellular regulator activity in vivo or in vitro. The test compounds can be macromolecules, such as biological polymers, including proteins, polysaccharides and nucleic acids. Sources of test compounds which can be screened for cellular regulator inhibitory activity include, for example, libraries of small organic molecules, peptides, polypeptides, DNA, and RNA. Additionally, test compounds can be preselected based on a variety of criteria. For example, suitable test compounds can be selected as having known inhibition or enhancement activity with respect to translation or proteasome function, for example. Alternatively, the test compounds can be selected randomly and tested by the screening methods of the present invention. Test compounds can be administered to the reaction system at a single concentration or, alternatively, at a range of concentrations to determine, for example, the optimal modulatory activity toward the cellular regulator.

The invention provides a method of identifying a ribozyme reactive with a cellular regulator of virus replication or expression. The method consists of: (a) introducing a randomized ribozyme library into a population of cells expressing a negative selection marker gene operatively linked to a viral nucleic acid element acted on by a cellular regulator of virus replication or expression; (b) subjecting said population of cells to negative selection, and (c) recovering one or more ribozymes from viable cells following said negative selection.

Also provided is a method of identifying a cellular regulator of virus replication or expression. The method consists of: (a) introducing a randomized ribozyme library into a population of cells expressing a negative selection marker operatively linked to a viral nucleic acid element acted on by a cellular regulator of virus replication or expression; (b) subjecting said population of cells to negative selection; (c) recovering one or more ribozymes from viable cells following said negative selection; and (d) sequencing the target recognition sequence of said recovered ribozyme to identify the nucleic acid encoding said cellular regulator.

By reference to a virus, or to HCV in particular, as an exemplary infectious agent amenable to the methods of identifying a ribozyme or a cellular regulator of the invention, one skilled in the art will readily know, in light of the teachings and description herein that such methods are applicable to essentially all infectious agents which require cellular regulators for continued life cycle propagation including, for example, Hepatitis A, Hepatitis G, rhinovirus and poliovirus. Therefore, the methods of identifying a cellular regulator, or ribozyme selective to a cellular regulator, as well as methods of treating an infectious disease once such regulators have been identified are applicable to a variety of infectious diseases including, for example, both DNA and RNA viral infections and parasitic diseases.

For the successful application of such methods, it is sufficient to have identified a nucleic acid derived from an infectious agent which is acted on by a cellular regulator. Once identified, the nucleic acid derived from the infectious agent can be operatively linked to a negative selection marker gene, for example, and subjected to negative selection using the methods of the invention.

Moreover, it is not necessary for the nucleic acid derived from the infectious agent to be unique to the replication or expression mechanism of that agent. Instead, the infectious agent derived nucleic acid acted on by a cellular regulator can include components or structures of cellular replication or expression elements and therefore overlap or be redundant with cellular machinery. The replication or expression efficiency of an infectious agent can rely on a balance between its own and cellular machinery for successful propagation. Therefore, decreasing the level or activity of cellular regulators acting on common components or structures can shift the balance toward utilization of cellular regulators for cellular functions at the expense of the infectious agent. An example of a nucleic acid acted on by a cellular regulator that includes a common component with cellular elements is a viral transcription promoter. Both the viral and cellular element are acted on by the RNA polymerase II cellular protein complex. A specific example of a nucleic acid acted on by a cellular regulator that is distinctive to an infectious agent is a viral IRES sequence because few cellular genes are expressed using this type of nucleic acid element.

The method of identifying a ribozyme reactive with a cellular regulator of virus replication, or it corresponding cellular regulator, involves the construction of a population of cells expressing a negative selection marker gene which is under the control, or operatively linked to a nucleic acid acted on by a cellular regulator of virus replication or expression. A specific example of such a cell population and its use is described further below in the Examples.

Briefly, the nucleic acid element acted on by a cellular regulator can be essentially any viral sequence found in cis on the viral nucleic acid but acted on in trans by a cellular regulator. A specific example, of such an element is the HCV IRES element. This element is also found in other flaviviruses as well as in rhinoviruses, encephalomyocarditis virus, foot-and-mouth disease virus, coxsackievirus and infectious bronchitis virus, for example, and as such, methods using cellular regulators identified for the HCV IRES element and therapeutic compounds thereto are applicable to all of the above-recited viruses and there corresponding diseases. Other elements can include, for example, viral promoters, enhancers and viral replication elements. Those skilled in the art will know what cis acting viral elements are applicable in the methods of the invention.

Cell populations containing cis acting nucleic acid element acted on by a cellular regulator are operatively linked to a negative selection marker gene. Operative linkage will depend on the type of element employed and is intended to refer to placing the viral element in an appropriate context and location in the reporter contruct as it would be found in its native genome. In the specific example of an IRES element, operative linkage places the element 3' to the transcription start site and 5' to the start codon. Similarly, operative linkage of a promoter element will be sufficiently upstream of the translation start codon to include sufficient 5' untranslated region sequence to effect translation in, for exmple, a CAP-dependent manner. The reportor constructs can be introduced into cell population using well known methods in the art and as described previously.

A negative selection marker can be a gene product that is, or can be made to be cytotoxic or cytostatic to cells. Specific examples include thymidine kinase (tk), cytosine deaminase (CD) and diphtheria toxin (DT). For example, the expression of these selection markers in cells is either toxic alone, or toxic in the presence of a selection compound which is metabolized by the marker gene product into a cytotoxic or cytostatic substance.

For example, ganciclovir is a purine nucleoside analogue having the structure [9-(1,3-dihydroxy-2-propoxy)methly] guanine. FIAU is a pyrimidine nucleoside analogue having the structure 1-(2"-deoxy-2'-fluoro-1-β-D-arabinofuranosyl-5-ido)uracil. These compounds are phosphorylated by the tk gene product, leading to their incorporation into replicated DNA during S phase, and subsequent cell death. Ganciclovir and FIAU are about 1000-fold better substrates for the Herpes simplex virus thymidine kinase (HSV-tk) compared to mammalian tk. Concentrations used for selection are between about 0.5–10 $\mu$M, and preferably about 2 $\mu$M for ganciclovir whereas FIAU concentrations are between about 0.05–1.0 $\mu$M, and preferably about 0.2 $\mu$M.

Negative selection with cytosine deaminase can employ, for example, the compound 5-fluorocytosine. This purine analogue is converted to 5-fluorouracil in the presence of cytosine deaminase which is incorporated into DNA, resulting in cell death. Concentrations used for 5-fluorocytosine are between about 50–250 $\mu$g/ml.

Finally, diphtheria toxin is itself toxic because it inhibits protein synthesis through NAD-dependent ADP-ribosylation of elongation factor 2 and therefore is a non-conditional marker gene. However, linkage of a diphtheria toxin gene to an inducible promoter or other regulatory element can make its expression conditional and therefore amenable to the methods of the invention.

Once negative selection proceeds, the surviving cells are those which express a ribozyme that is reactive with a cellular regulator required for replication or expression of the virus. The cells are isolated and the ribozymes are recovered using, for example, PCR or other well known methods in the art. The RST of the ribozyme is a sequence tag corresponding to a cellular regulator for virus replication or expression. Sequencing of this tag identifies the nucleic acid encoding the cellular regulator. Specific examples of RSTs corresponding to cellular regulators of the invention are set forth in FIG. 4D and as SEQ ID NOS:5–24, 72 and 73 and their corresponding TSTs are set forth as SEQ ID NOS:25–43. The function of four of these sequences have been determined. Specifically, SEQ ID NO:16 corresponds to the RST for human eIF2Bγ, the full length nucleotide and amino acid sequences of which is shown as SEQ ID NOS:1 and 2. SEQ ID NO:6 corresponds to the RST for human eIF2γ where as SEQ ID NOS:18 and 24 correspond to the RSTs for human proteasome alpha subunits PSMA1 and PSMA7, respectively.

The invention also provides a method of treating a HCV infection. The method consists of introducing a ribozyme selectively reactive with a RNA encoding a subunit of an eucaryotic translation initiation factor or a proteasome into a cell infected with HCV. Also provided is a method of treating HCV by introducing a ribozyme selectively reactive with a RNA encoding a cellular regulator corresponding to a RST selected from the group consisting of SEQ ID NOS:6–24. By substituting the ribozymes of the invention selectively reactive with a cellular regulator RNA with an antisense nucleic acid corresponding to a RST sequence selected from the group consisting of SEQ ID NOS:6–24, methods of treating a HCV infection are also provided. The antisense nucleic acids hybridize to the cellular regulator nucleic acid similar to catalytic ribozymes and inhibit transcription processing or translation of the RNA without subsequent cleavage. Such methods will be described below with reference to a ribozyme of the invention, but those skilled in the art will know that antisense nucleic acids can similarly be substituted for the ribozymes to prevent or reduce the severity of a HCV infection.

A ribozyme encoding any of the RST sequences set forth as SEQ ID NOS:6–24, or a combination thereof can be delivered in a wide variety of ways to HCV-infected or HCV-susceptible cells to interrupt or prevent HCV infection. The ribozyme can be administered as RNA or expressed from an expression vector. The ribozyme can be administered ex vivo by, for example, administering to cells that have been removed from an infected individual, and then returned to the individual, or the ribozyme can be administered in vivo. Delivery can be performed using any appropriate delivery vehicle known to those skilled in the art including, for example, a liposome, a controlled release vehicle, electroporation or covalently attached moieties, and other pharmacologically acceptable methods of delivery. A carrier can provide specificity for liver accumulation of the ribozyme at the liver which is the primary site of HCV infection. The ribozyme delivery vehicle can be designed to serve as a slow release reservoir or to deliver its contents directly to the target cell. Examples of ribozyme delivery vehicles include liposomes, hydrogels, cyclodextrins, biodegradable nanocapsules, and bioadhesive microspheres. Liposomes can readily be targeted to the liver for delivery of RNA to infected hepatocytes.

Routes of ribozyme administration include intramuscular, aerosol, intravenous, parenteral, intraperitoneal. Generally however, the route of administration will be through the portal vein since this is a direct route to the liver. The dosage of ribozyme will also depend on a variety of factors, such as the form of the ribozyme, the route of administration, the severity of infection or stage of disease, the general condition of the patient being treated, and thus can vary widely. Generally the dosage of ribozyme will be between about 10 μg-200 mg/kg of body weight per day and result in therapeutic or prophylactic levels within the targeted cells sufficient to inhibit or eradicate HCV from the cells. The duration of treatment may extend throughout the course of HCV infection or disease symptoms, usually at least about 7–30 days, with longer durations being necessary for severe infections. The number and timing of doses can also vary depending on, for example, the extent of infection A viral vector containing a ribozyme corresponding to a cellular regulator RST of the invention can be prepared in any of a wide variety of ways known to those skilled in the art. Representative retroviral vectors which can be used in the methods of the invention are described, for example, in U.S. Pat. Nos. 4,861,719, 5,124,263 and 5,219,740. Other vectors may also be employed, particularly for the ex vivo methods, such as DNA vectors, pseudotype retroviral vectors, adenovirus, and adeno-associated virus vectors.

The viral vector, consisting of infectious, but replication-defective, viral particles, which contain at least one DNA sequence encoding a ribozyme selectively reactive with a cellular regulator, is administered in an amount effective to inhibit or prevent HCV infection in a host. The vector particles may be administered in an amount from 1 plaque forming unit to about $10^{14}$ plaque forming units, more preferably from about $1 \times 10^6$ plaque forming units to about $1 \times 10^{13}$ plaque forming units. A sufficient number of vector particles containing a ribozyme selectively reactive with a cellular regulator of the invention is administered to the liver to infect up to at least about 50% of the hepatocytes, usually about 80%, preferably about 90%, or more of the hepatocytes in the individual. Subsequent administrations can be performed, as needed, to effectively treat or reduce the severity of the HCV infection.

Exemplary ribozymes of the invention include, for example, those having RST sequences set forth as SEQ ID NOS:6–24. Two of these RST sequences correspond to different translation initiation factor subunits, namely, eIF2Bγ and eIF2γ. Another two of these RST sequences correspond to different subunits of a proteasome complex, namely, proteasome alpha subunit PSMA1 and PSMA7. The RST sequences corresponding to these specific cellular regulators are set forth as SEQ ID NOS:6, 16, 18 and 24, respectively.

In addition to the methods of treating a HCV infection using ribozymes of the invention, inhibitory compounds identified by the screening methods described previously can similarly be used to reduce the severity of such an infection. Small organic compounds have particular advantage because of their ease of formulation and administration using well known methods in the pharmaceutical arts.

It is understood that modifications which do not substantially affect the activity of the various embodiments of this invention are also included within the definition of the invention provided herein. Accordingly, the following examples are intended to illustrate but not limit the present invention.

EXAMPLE I

Preparation of the Random Retroviral Vector Ribozyme Library

This example demonstrates the construction of a random retroviral plasmid ribozyme gene library. The inventors have discovered that by introducing a random retroviral plasmid ribozyme gene library into a HeLa cell cell line having a HSV thymidine kinase gene linked to an internal ribosome entry site (IRES), certain of the ribozymes will selectively target and inactivate mRNA molecules necessary for IRES-dependent translation. If the ribozyme has inactivated IRES-dependent translation, the HeLa cells will survive ganciclovir-mediated killing. The ribozyme genes are then rescued from the surviving colonies and sequenced across their substrate binding sites. The corresponding ribozyme binding sequence, or "ribozyme sequence tag" (RST) is a sequence present in an IRES-dependent translation regulator nucleic acid molecule targeted by the ribozyme. Thus, knowledge of the RST allows novel IRES-dependent translation regulator nucleic acids to be identified and isolated.

A plasmid-based retroviral library was constructed by inserting random ribozyme gene sequences into parent vector pLHPM-2 kb. pLHPM-2 kb contains 5' and 3' long terminal repeats (LTR) of the Moloney retroviral genome; a neomycin resistance gene driven by the LTR; an SV40 promoter driving a puromycin resistance gene; and a ribozyme transcription cassette containing a tRNAval promoter and a 2 kb stuffer insert. When the stuffer insert is removed and replaced by the random ribozyme library inserts, the tRNAval promoter can drive transcription of the inserted ribozyme gene.

To prepare the pLHPM-RzLib vector, plasmid pLHPM-2 kb was digested overnight at 65° C. with BstBI, phenol chloroform extracted and ethanol precipitated. The resuspended DNA was then digested overnight at 37° C. with MluI. This double digestion excises the 2 kb stuffer fragment. The resultant 6 kb plasmid vector DNA fragment was purified by agarose gel electrophoresis.

To prepare the random ribozyme library inserts, three oligonucleotides were synthesized and annealed in annealing buffer (50 mM NaCl, 10 mM Tris pH 7.5, 5 mM MgCl2) at a molar ratio of 1:3:3 (oligo1:oligo2:oligo3) by heating to 90° C. followed by slow cooling to room temperature. The three oligonucleotides had the following sequences:

Oligo1: 5'-cgcgtaccaggtaatataccacaacgtgtgtttctctggtnnn nttctnnnnnnnnggatcctgtttccgcccggttt-3' (SEQ ID NO:44)
Oligo2: 5'-cgttgtggtatattacctggta-3' (SEQ ID NO:45)
Oligo3: 5'-cgaaaccgggcggaaacagg-3' (SEQ ID NO:46)

To provide for random and uniform incorporation of A, T, C and G nucleotides at the positions represented as N nucleotides in oligo1, the A, T, C and G reagents were premixed, and the same mixture used for every N position in the oligonucleotide synthesis. The ribozyme insert library formed by annealing the three oligonucleotides (SEQ ID NOS:44–46) thus contains 8 positions with random nucleotides corresponding to helix 1 of the ribozyme, and 4 random positions with random nucleotides corresponding to helix 2 of the ribozyme.

In order to ligate the pLHPM-RzLib vector DNA fragment with the random ribozyme insert library, 0.5 pmole of the vector and an 8-fold molar excess of annealed oligonucleotides were ligated overnight with 10 units of T4 DNA ligase. Ultracompetent DH12S bacteria (Life Technologies) were then electroporated with the ligation mixture. Bacterial colonies containing the retroviral plasmid ribozyme library was obtained.

The bacterial colonies containing the retroviral plasmid ribozyme library were pooled in aliquots as a master stock and frozen at −80° C. Working stocks were made by culturing 1 ml of the master stock in 60 ml LB media overnight at 30° C. A 1 ml aliquot of the working stock was used to make a 500 ml bacterial culture by incubation at 30° C. overnight. Plasmid DNA was then extracted from the 500 ml culture and transfected into HF revertant cells, as described in Example II, below.

Following the cloning of the randomized hairpin ribozyme genes into pLHPM, the "randomness" of the plasmid library was evaluated by both statistical and functional analyses. A complete ribozyme library of this design, with 12 random positions, would contain $4^{12}$, or $1.67 \times 10^7$, different members. For the statistical analysis, sixty individual bacterial transformants were picked and sequenced. This allowed an evaluation of the complexity of the library without having to manually sequence each library member. The statistical "randomness" of the library was determined utilizing the formula for a two-sided approximate binomial confidence interval: $E=1.96*\text{squareroot}(P*(1-P)/N)$, where P=the expected proportion of each nucleotide in a given position (this value for DNA bases equals 25% or P=0.25), E=the desired confidence interval around P (i.e. P+/−E) and N=the required sample size (Callahan Associates, Inc., La Jolla, Calif.). To determine the proportion of each base within 5% (E=0.05), the required sample size is 289. Since each ribozyme molecule contains twelve independent positions, the number of individual ribozyme genes that need to be sequenced out of the library equals 289 divided by 12, or about 25 molecules.

For a functional evaluation of the library's complexity, in vitro cleavage was utilized to determine if ribozymes that target known RNA substrates were present in the library pool. This involved in vitro transcribing a comparable ribozyme library in one reaction and then testing the pool's ability to cleave a variety of different RNA substrates. Several different short RNA targets were properly and efficiently cleaved by the in vitro transcribed library. This qualitative analysis suggested a significantly complex library of ribozyme genes.

Viral vector was produced from the ribozyme library plasmid using a triple transfection technique. CF2 cells were seeded at $3.5 \times 10^4$ cells/cm$^2$ one day prior to transfection. The cells were transfected with a 1:1:1 mixture of the ribozyme library plasmid or control ribozyme plasmid, a plasmid encoding the moloney murine virus gag-pol genes, and a plasmid encoding the vesicular stomatitis virus-G gene, using the cationic lipid TransIT-LT1 (Pan Vera Corporation). $7.8 \times 10^6$ cells were transfected with 25 µg of each plasmid complexed with 250 ml of the lipid in a total volume of 20 µl of serum free media. After 6 hours, the media was replaced with growth media. The cell supernatant containing retroviral particles was collected every 24 hours beginning on day 2 after addition of fresh media. The supernatant was filtered through 0.4 µm filters and titered in a standard assay using HT1080 cells.

EXAMPLE II

Isolation of Ribozymes that Target IRES-dependent Translation Factors

This example demonstrates the isolation of ribozyme genes that confer ganciclovir (GCV) resistance by inactivating IRES-dependent translation, and the identification of the nucleic acid sequences they target.

The Hela cell line used in these experiments was modified with a bicistronic reporter gene that confers hygromycin B resistance and GCV resistance. The bicistronic reporter gene pHyg-5'tk was constructed with the SV40 promoter driving the expression of hygromycin B phosphotransferase and the 5' untranslated region of HCV (nucleotides (nt) 38–341) upstream of HSV thymidine kinase (HSV-tk, see FIG. 1). The 5' nontranslated region of hepatitis C virus (HCV)

functions as an internal ribosome entry site (IRES) and is essential for translation of HCV proteins. Transcription of the 5' nontranslated region allows for IRES-mediated translation of HSV-tk, which converts GCV to the monophosphate which is further metabolized to the triphosphate a cytotoxic analog of GTP. Cells that express ribozymes whose target mRNAs encode proteins necessary for IRES-dependent translation will no longer synthesize HSV-tk and therefore will survive GCV selection.

In the synthesis of pHyg-5'tk, the hygromycin B phosphotransferase gene was amplified from pIRES hygro (Clontech) by PCR with oligonucleotide primers P1 (5'-ggatgatgaagacatacaaggagacgaccttccatggatagatccggaaagcct-3') (SEQ ID NO:66 and P2 (5'-gtcggcatgtcgactattcctttgccctcggacg-3') SEQ ID NO:67, then digested with BbsI and SalI and used to replace the puromycin-resistance gene in pPur-HCV (Welch, et al., 1996) after digestion with BsmBI and SalI to generate pHyg-5° C. The herpes simplex virus thymidine kinase gene was amplified by PCR with primers P3 (5'-cgatcgtagaattcaggtctcgtagaccgtgcaccatggcttcgtacccctgccatc aacacgcgtctgcgttcgaccaggct-3') SEQ ID NO:68 and P4 (5'-gtacccgattatgatctcagttagcctccccatctcccg-3') SEQ ID NO:69 from pcHytk, then digested with BsaI and BsaBI and inserted into pHyg-5° C. following digestion with BsaI (partial) and BsaBI (to completion) to generate pHyg-5'tk.

Translation of HSV-tk-mediated by HCV 5'UTR (cap-independent, HCV nucleotides 38–341) was confirmed by Western blotting analysis of the tk protein. The vector was designed such that the authentic HCV Core protein translation start site (AUG at position 342 of the viral RNA) serves as the translation initiation site for the tk gene. The functional activity of tk was determined by administration of GCV to the cell culture medium. Continuous GCV application (10–100 uM) resulted in complete cell death, whereas untransfected HeLa cells or cells transfected with a similar vector construct expressing Core protein in place of the tk gene remained unaffected by GCV application. To confirm that tk expression was mediated by HCV IRES and not from read-through translation of the hygromycin gene, two control plasmids were generated that were identical to the parental, except for deletion of part of the 5'UTR necessary for IRES function. A reporter cell line was generated by electroporation of HeLa cells with pHyg-5'tk and selected with 250 μg/ml hygromycin. Single cell clones of stable HSV-tk expressing cells (HeLa 5'tk cells) were obtained according to standard limited dilution cloning techniques and functionally characterized for GCV-mediated cell killing.

Following clonal expansion, several stable HeLa 5'tk clones were characterized for GCV killing and a particular HeLa 5'tk clone was selected that was completely killed following exposure to 20 uM GCV. HSV-tk-negative cells were then added into HeLa 5'tk cells to determine the rate of killing of tk positive cells and recovery of tk negative cells and determined the optimal concentration and exposure time of GCV as well as established conditions with minimized "bystander" effect (toxicity to neighboring cells not expressing the HSV-tk gene). The optimal concentration of GCV was determined to be 10–40 uM, applied for 24 to 40 hours after reattachment of the cells after plating. The optimal cell plating density was determined to be $0.4 \times 10^4$ cells/cm$^2$.

Retroviral vectors expressing a neo$^R$ marker and either a control ribozyme or a library of ribozymes with randomized target recognition sequences were used to stably transduce clonal populations of these reporter cells, which were then subjected to GCV selection (FIG. 2). Hela cells were cultured at 37° C. in DMEM (Gibco BRL) supplemented with 10% FBS, L-gln, sodium pyruvate and antibiotics. Retroviral library transduction was performed on clonal HeLa 5'tk cells in sixteen 225 cm$^2$ cell culture flasks using a total of 460 ml of non-concentrated retroviral supernatant (titer $4 \times 10^5$ CFU/ml determined on HeLa cells, MOI 2). Control retroviral transduction (total volume 40 ml, titer $2 \times 10^4$ CFU/ml) was performed in two 225 cm$^2$ cell culture flasks. 24 hours post transfection, cells were selected with G418 (500 μg/ml) for two weeks.

Figure 3:
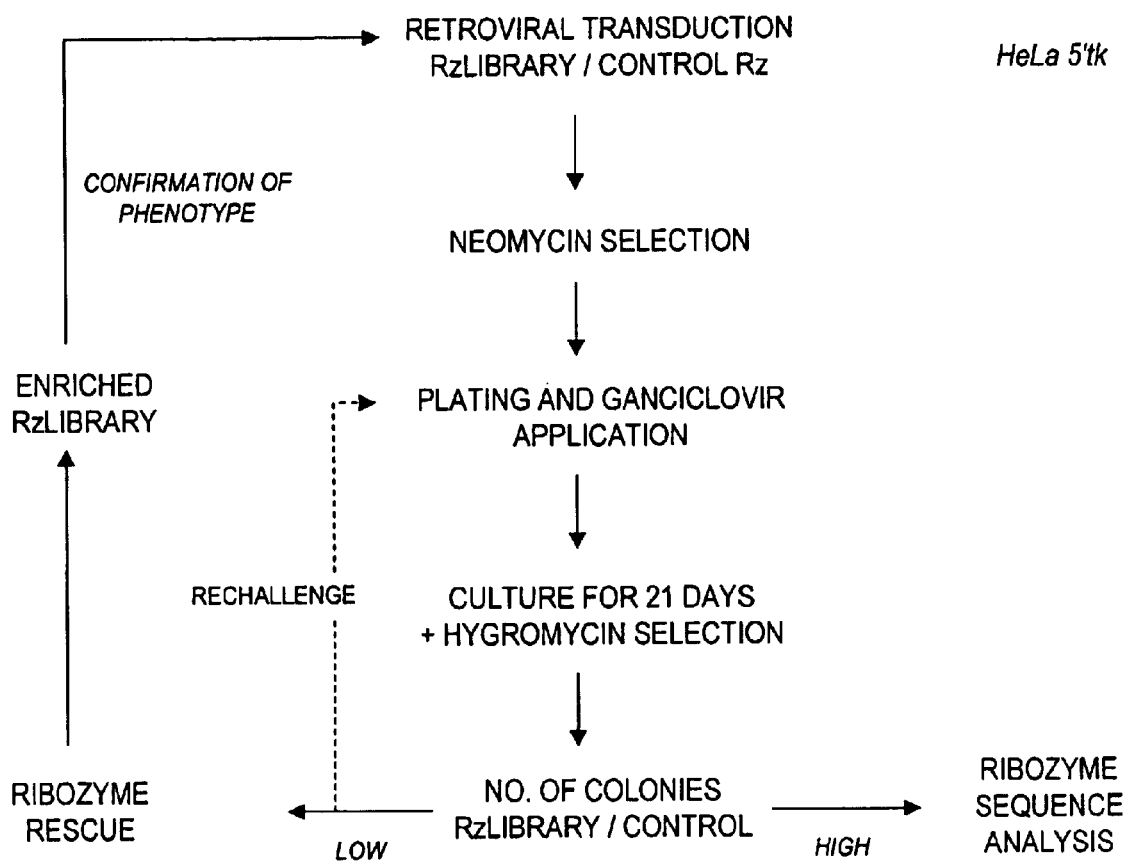
FIG. 3 shows a flow chart of the tissue culture selection system for the discovery of HCV IRES regulator molecules.

Following G418 selection, ribozyme library transduced cells were seeded at a density of $0.4 \times 10^4$/cm$^2$. This plating density was chosen after optimization studies in order to minimize a potential "bystander" effect. Cells were exposed to GCV at a concentration of 40 μM for 24 h or 40 h and subsequently cultured under hygromycin selection (250 μg/ml) for 21 days (FIG. 3, showing a schematic of the selection system).

Figure 4A:
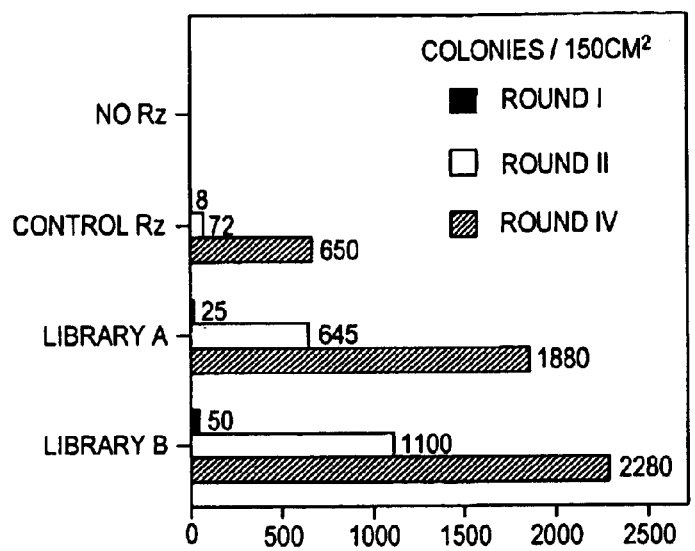
FIG. 4 shows the selection of 5'tk cells with a GCV-resistant phenotype following transduction with the retroviral hairpin ribozyme library.
FIG. 4d shows SEQ ID NOS:5–24, 72 and 73, respectively, in order of appearance.

Following one round of GCV selection for 40 hours, 25 colonies were obtained in the library transduced cell population versus 8 in the control vector transduced population and 0 in the untransduced population. Library transduced cells exposed to GCV for 24 hours produced 50 resistant colonies (FIG. 4A).

The method of Rz gene rescue was performed by PCR amplification of the genomic DNA from the cultured cells, followed by batch recloning of the Rz genes into the pLHPM vector. PCR rescue was performed on genomic DNA, isolated from the selected cells using the QIAamp Blood Kit (Qiagen, Valencia, Calif.). PCR amplification with primers LHPM-2878 (5'-ggcgggactatggttgctgactaat-3') SEQ ID NO:70 and 5'MFT2 (5'-ggttatcacgttcgcctcacacgc-3') SEQ ID NO:71 were used o amplify a 300 bp fragment containing the ribozyme genes using the PCR protocol of 35 cycles at 94° C. for 20 sec, 65° C. for 30 sec, and 72° C. for 45 sec; terminal extension was performed at 72° C. for 7 min. The PCR product, which contained a pool of Rz genes, was then digested with BamHI and MluI and ligated into pLHPM digested with the same enzymes. Ho et al. NAR 24:901–907 (1996). The resulting plasmid was used to generate enriched ribozyme library retroviral vector by triple transfection as described previously.

The HeLa Hyg 5' tk cell line was subjected to three additional rounds of transduction, puromycin selection, GCV exposure, and rescue of ribozyme sequences. Enhanced colony formation was seen at each round of selection (FIG. 4A). Following the four rounds of selection, the sequences of these rescued ribozyme were determined using primer NL6H6 by standard techniques. The resultant gene sequences of ribozymes that conferred GCV resistance were:

HVC1:AGCTGGCAGAACTGCaccagagaaacacacgttgtgg tacattacctggta (SEQ ID NO: 47)
HCV2:TTCGTCAAAGAATTCTaccagagaaacacacgttgtg gtacattacctggta (SEQ ID NO: 48)
HCV3:GCGATCTAAGAATCAGaccagaqaaacacacgttgtgg tacattacctggta (SEQ ID NO: 49)
HCV4:CTAACTTTAGAAACTAaccagagaaacacacgttgtg gtacattacctggta (SEQ ID NO: 50)
HCV5:CTTGCGCGAGAACATCaccagagaaacacacgttgtg gtacattacctggta (SEQ ID NO: 51)
HCV6:TTCTTATTAGAAAGCTaccagagaaacacacgttgtggt acattacctggta (SEQ ID NO: 52)
HCV7:TCGCTTAAAGAAGGAAaccagagaaacacacgttgtg gtacattacctggta (SEQ ID NO: 53)
HCV8:AGCCGAGGAGAATCCCaccagagaaacacacgttgtg gtacattacctggta (SEQ ID NO: 54)

HCV9:AGCCGCATAGAAGCAGaccagagaaacacacgttgtg gtacattacctggta (SEQ ID NO: 55)
HCV10:TAATTATTAGAATGCGaccagagaaacacacgttgtgg tacattacctggta (SEQ ID NO: 56)
HCV11:AGACCAAAAGAAGCTTaccagagaaacacacgttgt ggtacattacctggta (SEQ ID NO: 57)
HCV12:ACAGCCAGAGAAACCGaccagagaaacacacgtt gtggtacattacctggta (SEQ ID NO: 58)
HCV13:TTAAACGCAGAATACGaccagagaaacacacgttgt ggtacattacctggta (SEQ ID NO: 59)
HCV14:TATTGGCTAGAACGAAaccagagaaacacacgttgtg gtacattacctggta (SEQ ID NO: 60)
HCV15:TCAGCCTCAGAACTGCaccagagaaacacacgttgt ggtacattacctggta (SEQ ID NO: 61)
HCV16:TTGTTAATAGAAACTTaccagagaaacacacgttgtg gtacattacctggta (SEQ ID NO: 62)
HCV17:TAACACGTAGAAAGACaccagagaaacacacgttgt ggtacattacctggta (SEQ ID NO: 63)
HCV18:CTGTCAACAGAACTCGaccagagaaacacacgttgt ggtacattacctggta (SEQ ID NO: 64)
HCV19:ATTCATATAGAATGGAaccagagaaacacacgttgtg gtacattacctggta (SEQ ID NO: 65)

Figure 4B:
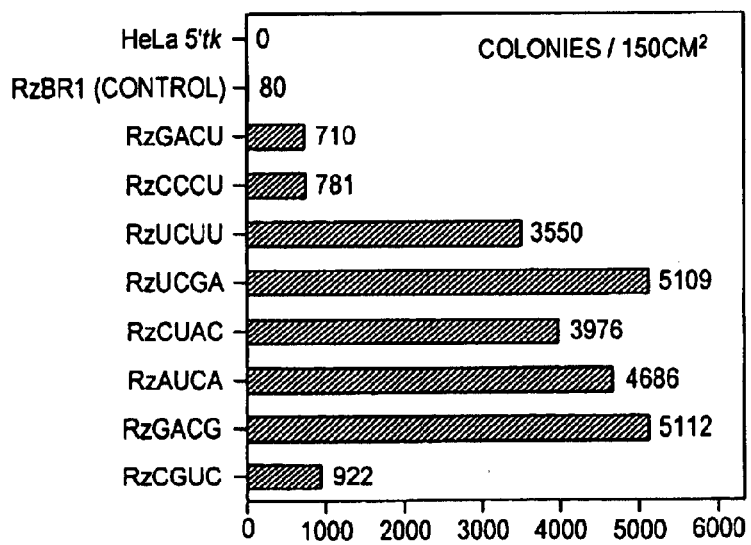
Figure 4C:
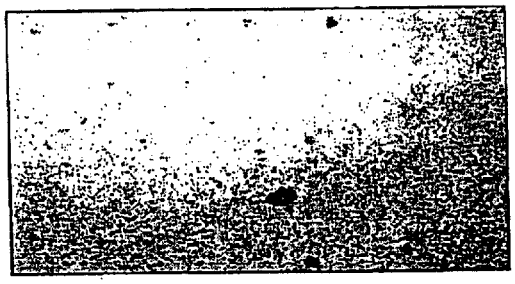
Figure 4C:
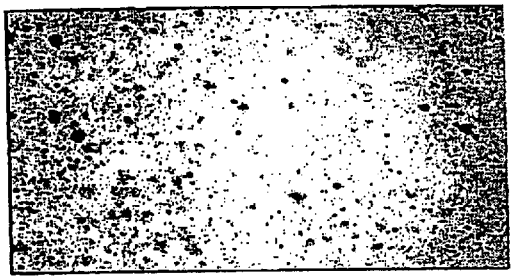
Figure 4C:
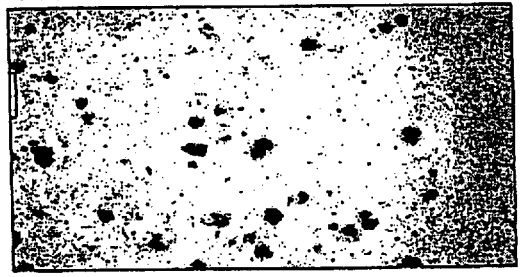
Figure 4C:
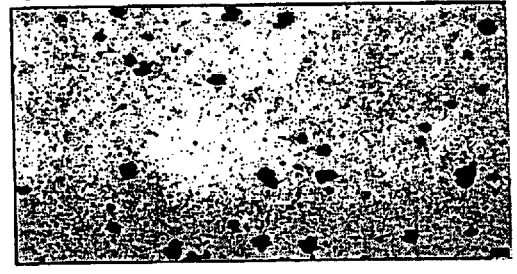

Introduction of these individual ribozymes into the HeLa 5'tk selection system again resulted in enhanced colony formation compared to control. FIG. 4B shows the number of colonies following transduction with individual ribozymes and FIG. 4C shows appearance of colonies following selection with ribozymes 2, 6 and 9. FIG. 4D shows the RST region of each of the above ribozymes as well as the corresponding target genes that have been identified (SEQ ID NOS:5 through 24, 72 and 73, respectively).

To verify that the rescued ribozymes act as enzymes and derived phenotypes are not due to anti-sense or aptimer effects, a catalytically inactive version of a ribozyme can be prepared and tested using the functional assay as described above. A triple mutation in the catalytic core of HCV4 and HCV6 were generated by replacing the AAA sequence of loop 2 with a UGC sequence to disable the ribozyme (FIG. 2). These changes eliminate the catalytic activity of the ribozyme without altering the target binding sequences. The disabled versions of HCV4 and 6 did not significantly increase the number of GCV resistant colonies over background indicating that the phenotypic changes observed with HCV 4 and 6 are likely due to ribozyme-catalyzed hydrolysis and not aptimer or antisense effects.

EXAMPLE III

Isolation and Characterization of Genes that Promote HCV-IRES Function

This example demonstrates the isolation of full-length nucleic acid molecules that promote IRES function as a translation initiator and determination of the correpsonding cDNA and polypeptide sequences.

Since ribozymes recognize their cognate targets by sequence complementarity, the sequence of a ribozyme that causes a phenotype through its catalytic activity predicts a sequence tag that can be used to clone the target gene. This "Ribozyme Sequence Tag" or RST is 16 bases long, consisting of the two target binding arms (helix 1 and 2) and the requisite GUC in the target (FIG. 2). The RST can thus be used as a primer for 3' and 5' RACE.

Specifically, 3'-RACE can be used to amplify a cDNA fragment which contains the a sequence with homology to the inferred substrate bing site of a ribozyme. mRNAs (2 µg) were extracted from GCV selected HeLa 5'tk cells and a first strand cDNA was synthesized from the mRNA with avian myeloblastosis. virus reverse transcriptase and a modified lock-docking oligo(dT) primer (Clontech) according to the manufacturers recommendations (Marathon cDNA amplification kit, Clontech). The product of this reaction was used as a template in a second strand synthesis reaction. After ligation of the double-stranded cDNAs with the Marathon cDNA adaptor, 3'-RACE amplification was performed using the double-stranded cDNA as a template with a sense primer derived from the sequence of the substrate binding domain of a rescued ribozyme gene and an adaptor specific primer, AP1 (Clontech). The resulting PCR products were then cloned and sequenced. Since the ribozyme specific primer is incorporated into the PCR product, the exact sequence to which the primer bound during PCR is determined by 5' RACE using upstream sequences to generate a 5' RACE anti-sense primer.

For 5'RACE, mRNAs (2 µg) extracted from GCV selected HeLa 5'tk cells and cDNA was synthesized with avian myeloblastosis virus reverse transcriptase and a modified lock-docking oligo(dT) primer (Clontech) according to the manufacturers recommendations (Marathon cDNA amplification kit, Clontech). After ligation of the double-stranded cDNAs with the Marathon cDNA adaptor, 5'-RACE amplification was performed using the double-stranded cDNA as a template with a anti-sense primer derived from the sequence of the substrate binding domain of the ribozyme and an adaptor specific primer, AP1 (Clontech). The resulting PCR product can then cloned and sequenced. Since the ribozyme specific primer is incorporated into the PCR product, the exact sequence to which the primer bound during PCR is determined by 3' RACE using upstream sequences to generate a sense 3' RACE primer. In addition, gene-specific primers were generated based on the sequences of progressively amplified 5' products. Finally, the 5'-terminus of the gene was cloned using a SMART amplification technique (Clontech). PCR-amplified cDNA fragments were cloned into T/A-type PCR cloning vectors (pCR2.1; Invitrogen) and sequenced.

5'-RACE was used to amplify a cDNA fragment which contains a sequence with homology to the inferred substrate bing site of the ribozyme, HCV6. 5'-RACE amplification was performed using the double-stranded cDNA as a template with a anti-sense primer derived from the sequence of the substrate binding domain of HCV6 (5' ttcttattgacnagct3' SEQ ID NO:74). Identified was a 580 bp 5' fragment sharing homology to the rat eIF2B gamma subunit gene (eIF2Bγ) (GenBank accession number U38253). To obtain the terminal 5' nucleotides of the mRNA, SMART PCR amplification was performed with oligo(dT) as a primer for reverse transcription.

To identify RNAs which can be specifically cleaved by a particular ribozyme, a 3' RACE technique was developed which preferentially amplifies the 3' product of an in vitro cleavage reaction. Approximately 1 ug of mRNA is incubated with 300 ng of a specific ribozyme in conditions which support ribozyme cleavage (10 mM Tris HCl, 12 mM MgCl2, 37C). cDNA was then synthesized using an Superscript reverse transcriptase (Life Technologies), and an anchored oligo-dT primer for reverse transcription followed by second strand synthesis using a SMART primer (Clontech). This resulted in the addition of SMART primer sequences to the 5' end of the cDNAs including any cDNAs generated from 3' ribozyme cleavage products. The cleavage products were then preferentially PCR amplified by using a 5' primer which includes sequences found in the SMART oligo as well as bases which include the NGUC ribozyme cleavage site. Compared with the 5' end obtained from the 5' RACE amplification, we were able to obtain an additional 88 nucleotides of 5' sequence.

Figure 5C:
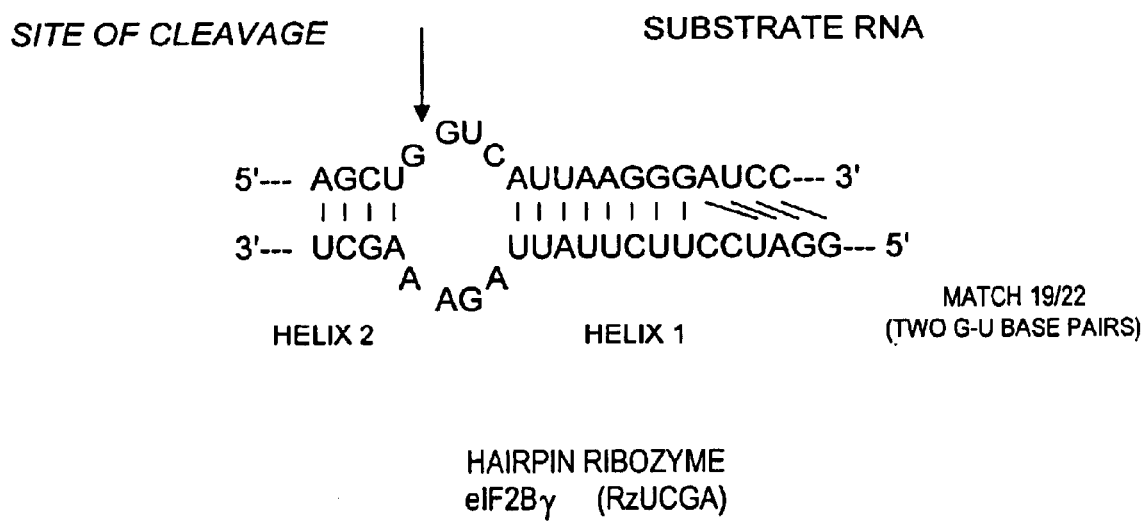
FIG. 5C shows that ribozyme RzUCGA (SEQ ID NO:144) targets human eukaryotic initiation factor 2B gamma subunit (eIF2Bγ) mRNA (SEQ ID NO: 143) (RzUCGA and the eIF2Bγ mRNA are shown as segments of the larger molecule).

Based on this sequence information, the entire human eIF2Bγ gene was cloned (FIG. 5A), which encodes a protein of 452 amino acids, with 91% identity to the rat protein (FIG. 5B). The putative RzHCV6 binding site contains one mismatch and two G-U base pairs in helix 1 of the Rz binding domains (FIG. 5C).

Target binding sequences, which are inferred from the sequences of rescued ribozymes, can also be used to query nucleotide databases. Using a BLAST search, the binding sequence of HCV4 partially matched a sequence within the gamma subunit of human eIF2 (GenBank accession number L19161. As this is a known gene, no further cloning was necessary.

Ribozymes can also be used to identify genes by radio-labeled oligonucleotide screening of CDNA libraries. $^{32}$p labeled oligonucleotides which correspond to the inferred cleavage sites of rescued ribozymes HCV8 have been used to screen cDNA libraries by means of standard filter hybridization methods.

EXAMPLE IV

Validation of Gene Function

This example shows that knockdown of eIF2Bγ or eIF2γ mRNA by several different gene targeted ribozymes confers GCV resistance in HeLa 5'tk cells, confirming that these genes are regulators of IRES mediated translation.

Figures 6A, 6B:
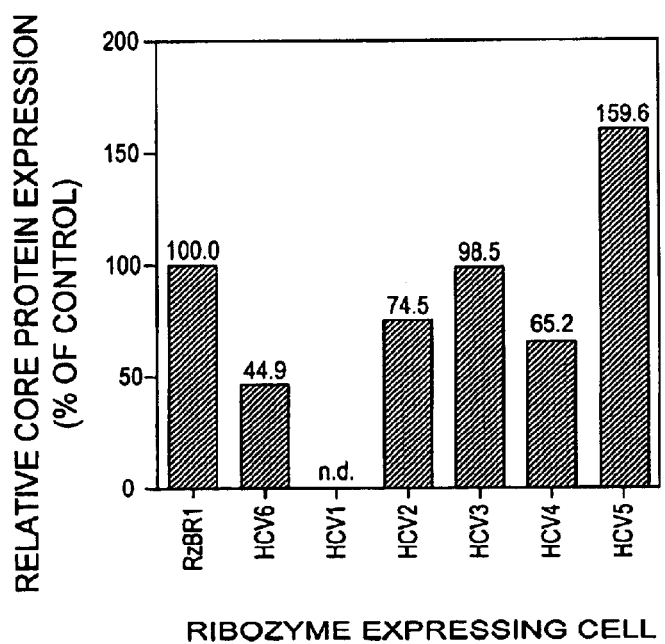
FIG. 6 shows quantitation of RNA transcripts in HeLa 5'tk cells by RNA blot analysis.

To confirm eIF2Bγ as a target gene involved in GCV resistance and HCV core protein expression, five validation ribozymes were designed (TVRz1–5) that were directed against additional GUC sites in the human eIF2Bγ mRNA. The nucleotide sequences of these validation ribozymes are shown below in Table 1 along with other eIF2Bγ TST sequences. (SEQ ID NOS: 75 through 95, respectively). These validation ribozymes were cloned into retroviral vectors for transduction of HeLa 5'tk cells. TVRz2–5 conferred greater than 10-fold increase in GCV-resistant colonies compared with the control. The results are shown in FIGS. 6A and B.

TABLE 1

GUC sites for human eIF2Bγ

| position | sequence | Vrz No. |
|---|---|---|
| 80 | CAGC GGUC UGACCCGG (SEQ ID. NO:75) | |
| 81 | AAGA AGUC AUUGUGGU (SEQ ID. NO:76) | 1 |
| 82 | CCC GGUC AAAAGGGG (SEQ ID. NO:77) | |
| 83 | AGCU GGUC AUUAGGG (SEQ ID. NO:78) | 2 |
| 84 | CACG GGUC UUGUGGAU (SEQ ID. NO:79) | 3 |
| 85 | AAUG GGUC AAUAACUU (SEQ ID. NO:80) | 4 |
| 86 | CUGA AGUC CUUAGAUA (SEQ ID. NO:81) | |
| 87 | UGCC UGUC GAGGAGAC (SEQ ID. NO:82) | |
| 981 | GACU UGUC CAGAUCAC (SEQ ID. NO:83) | |
| 1006 | GCUA UGUC CACAUCAU (SEQ ID. NO:84) | |
| 1007 | UUGC UGUC UGCUCUCU (SEQ ID. NO:85) | |
| 1008 | UCUC UGUC CAGAAGAA (SEQ ID. NO:86) | |
| 1009 | CACC AGUC CAUUCGUC (SEQ ID. NO:87) | |
| 1010 | CAUU CGUC AGCCCAGA (SEQ ID. NO:88) | |
| 1011 | AGAU UGUC AGCAAACA (SEQ ID. NO:89) | |
| 1012 | GAGA AGUC AUCCAUUA (SEQ ID. NO:90) | 5 |
| 1013 | GCUC AGUC AUUGGCUC (SEQ ID. NO:91) | |
| 1014 | AUCC UGUC UCAUAAAA (SEQ ID. NO:92) | |

TABLE 1-continued

GUC sites for human eIF2Bγ

| position | sequence | Vrz No. |
|---|---|---|
| 1015 | ACUC AGUC ACUGUGGA (SEQ ID. NO:93) | |
| 1016 | GCAG UGUC AUCUGCAA (SEQ ID. NO:94) | |
| 1017 | AGCA AGUC AGACUCCU (SEQ ID. NO:95) | |

Figure 7:
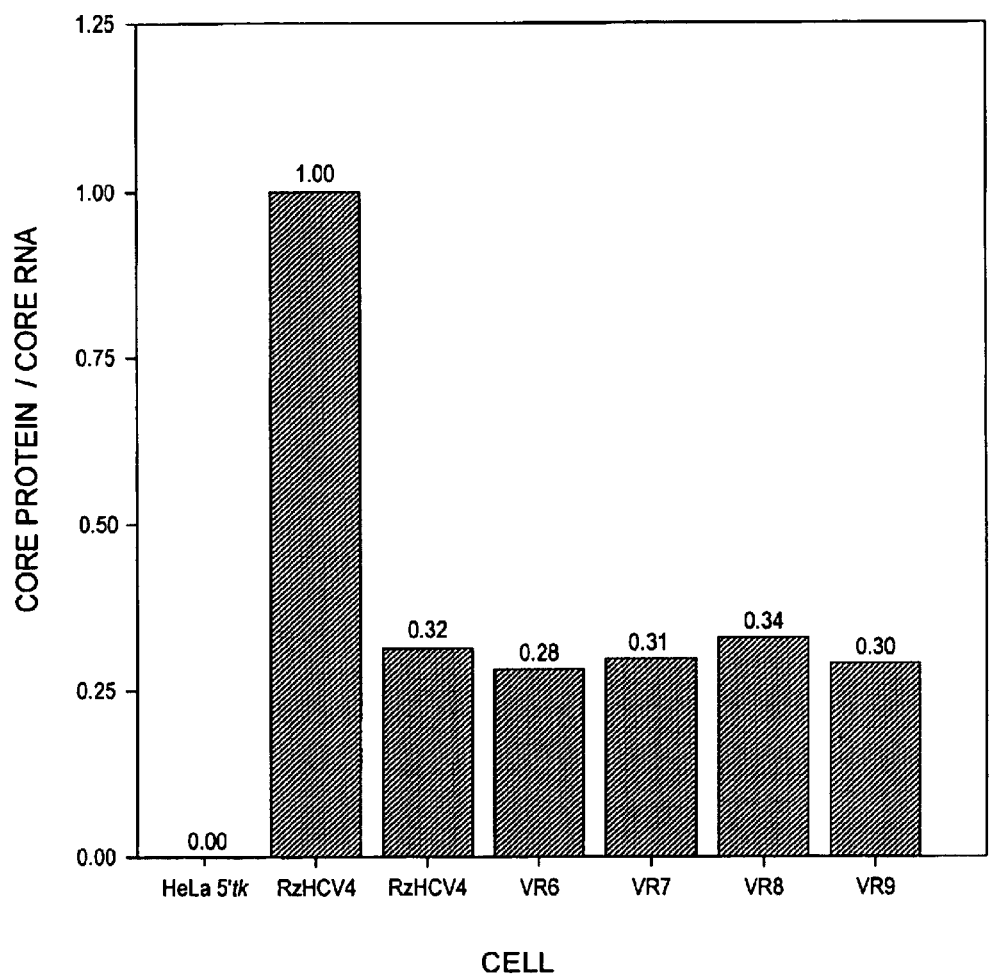
FIG. 7 shows the confirmation of human eIF2Bγ as a target gene involved in HCV IRES-mediated expression of herpes simplex virus thymidine kinase.

Validation ribozymes were also constructed against four potential cleavage sites in the eIF2γ mRNA (TVRz6–9). The nucleotide sequences of these validation ribozymes are shown below in Table 2 along with other eIF2γ TST sequences. Transduction of HeLa 5'tk cells with retroviral vectors expressing these ribozymes induced greater than 9-fold increase in the number of GCV-resistant colonies relative to the control (FIG. 7A).

TABLE 2

GUC sites for human eIF2γ

| position | sequence | Vrz No. |
|---|---|---|
| 50 | UUCG CGUC AGGAUCUC (SEQ ID. NO:96) | |
| 143 | AAUU GGUC AUGUAGCU (SEQ ID. NO:97) | 6 |
| 169 | CCAC AGUC GUCAAAGC (SEQ ID. NO:98) | |
| 172 | CAGU CGUC AAAGCUAU (SEQ ID. NO:99) | 7 |
| 199 | AUAC UGUC AGGUUCAA (SEQ ID. NO:100) | 8 |
| 379 | AAUU AGUC AGACAUGU (SEQ ID. NO:101) | 9 |
| 404 | UGAC UGUC CUGGCCAC (SEQ ID. NO:102) | |
| 593 | AGAA AGUC AGGCUAAA (SEQ ID. NO:103) | |
| 631 | CAUU UGUC CAAGGUAC (SEQ ID. NO:104) | |
| 790 | UUGA UGUC AACAAACC (SEQ ID. NO:105) | |
| 1004 | AGGC GGUC UUAUUGGA (SEQ ID. NO:106) | |
| 1083 | GUGC AGUC GGAGCUUU (SEQ ID. NO:107) | |
| 1194 | AAGC UGUC UAAGAAUG (SEQ ID. NO:108) | |
| 1233 | UCCC UGUC AACAGGAG (SEQ ID. NO:109) | |
| 1258 | GUGC UGUC AAGGCCGA (SEQ ID. NO:110) | |
| 1370 | UUGG GGUC AGAUAAGA (SEQ ID. NO:111) | |

Two other known genes were identified as TSTs from the library screen. HCV2 corresponds to human proteasome alpha subunit 1 PSMA1. HCV9 corresponds to human proteosome alpha subunit 7 PSMA7. The TST nucleotide sequences for the human PSMAI and PSMA7 cellular regulators for target validation ribosymes are shown below in Table 3.

TABLE 3

| position | sequence |
|---|---|
| | GUC sites for human PSMA1 |
| 133 | AUGA UGUC ACUGUUUG (SEQ ID. NO:112) |
| 215 | AGUU UGUC UGAAAUCA (SEQ ID. NO:113) |
| 371 | UAUG CGUC AGGAGUGU (SEQ ID. NO:114) |
| 420 | CCUG UGUC UCGUCUUG (SEQ ID. NO:115) |
| 425 | GUCU CGUC UUGUAUCU (SEQ ID. NO:116) |
| 497 | UGUU GGUC UCCUUAUU (SEQ ID. NO:117) |
| 548 | AACC UGUC CAUCGCU (SEQ ID. NO:118) |
| 633 | CAUA UGUC UGAAUUUA (SEQ ID. NO:119) |
| 677 | ACAU GGUC UGCGUGCC (SEQ ID. NO:120) |
| 792 | GAUG UGUC UCCAUUCC (SEQ ID. NO:121) |
| 809 | GGAA GGUC UUGAAGAA (SEQ ID. NO:122) |
| 909 | AGCC AGUC UAUAUAUG (SEQ ID. NO:123) |
| 1028 | AAUC AGUC CAGAUGUG (SEQ ID. NO:124) |
| 1099 | AAAG GGUC UGUAUAAU (SEQ ID. NO:125) |
| 1165 | UAGG UGUC UUUGUGGU (SEQ ID. NO:126) |

TABLE 3-continued

| position | sequence | | | |
|---|---|---|---|---|
| | GUC sites for human PSMA7 | | | |
| 49 | UCAC | CGUC | UUCUCGCC | (SEQ ID. NO:127) |
| 100 | AGGC | CGUC | AAGAAGGG | (SEQ ID. NO:128) |
| 168 | AAGA | AGUC | AGUGGCCA | (SEQ ID. NO:129) |
| 229 | ACAA | CGUC | UGCAUGGC | (SEQ ID. NO:130) |
| 271 | GGAU | AGUC | AUCAACAG | (SEQ ID. NO:131) |
| 328 | ACCC | GGUC | ACUGUGGA | (SEQ ID. NO:132) |
| 362 | CGCC | AGUC | UGAAGCAG | (SEQ ID. NO:133) |
| 522 | GCCA | AGUC | AGUGCGCG | (SEQ ID. NO:134) |
| 624 | GUUC | AGUC | AGGUGGCA | (SEQ ID. NO:135) |
| 652 | UUGC | UGUC | AUGAGGCG | (SEQ ID. NO:136) |
| 782 | AAAA | UGUC | UUUGCUUG | (SEQ ID. NO:137) |
| 824 | GAUG | AGUC | UCGAUGUG | (SEQ ID. NO:138) |
| 868 | UGAG | UGUC | CUACAAUA | (SEQ ID. NO:139) |

To ensure that the above-described validation ribozymes did not interfere with the transport or metabolism of GCV, their effects were evaluated on IRES-mediated HCV core protein translation from the cassette within the retroviral vector (pLHPM). Upon construction of the retroviral vector pLHPM a cassette translating the HCV Core protein via the HCV IRES was placed into the 3' part of the LTR transcript. Thereby, cells transduced with the library or single Rz candidates could be analyzed for the HCV Core protein expression by Western blotting. Western blotting was performed on protein lysates using an enhanced chemiluminescent blotting detection kit (Novex), and anti-HCV core monoclonal antibody (6C7 provided by Harry Greenberg, Stanford University). Blots were exposed to film and band intensities measured using a phosphoimager and ImageQuant software. After establishment of a linear relationship of the amount of Core protein and the measured signal (data not shown), GCV resistant colonies derived from the single Rz transduction were analyzed for HCV Core protein. Band volumes of HCV Core protein in Western blotting were analyzed by densitometry, normalized towards beta-actin and expressed as percentage relative to the control (RzBR1).

Figure 8A:
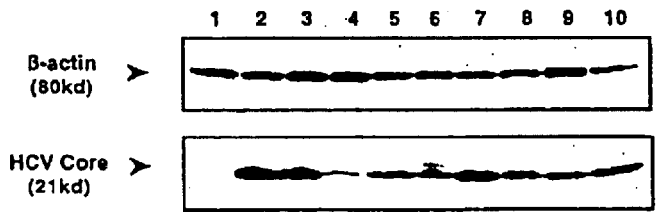
FIG. 8 shows a protein blot analysis of HCV Core protein of GCV-resistant colonies following transduction of single ribozymes into 5'tk cells.
Figure 8B:
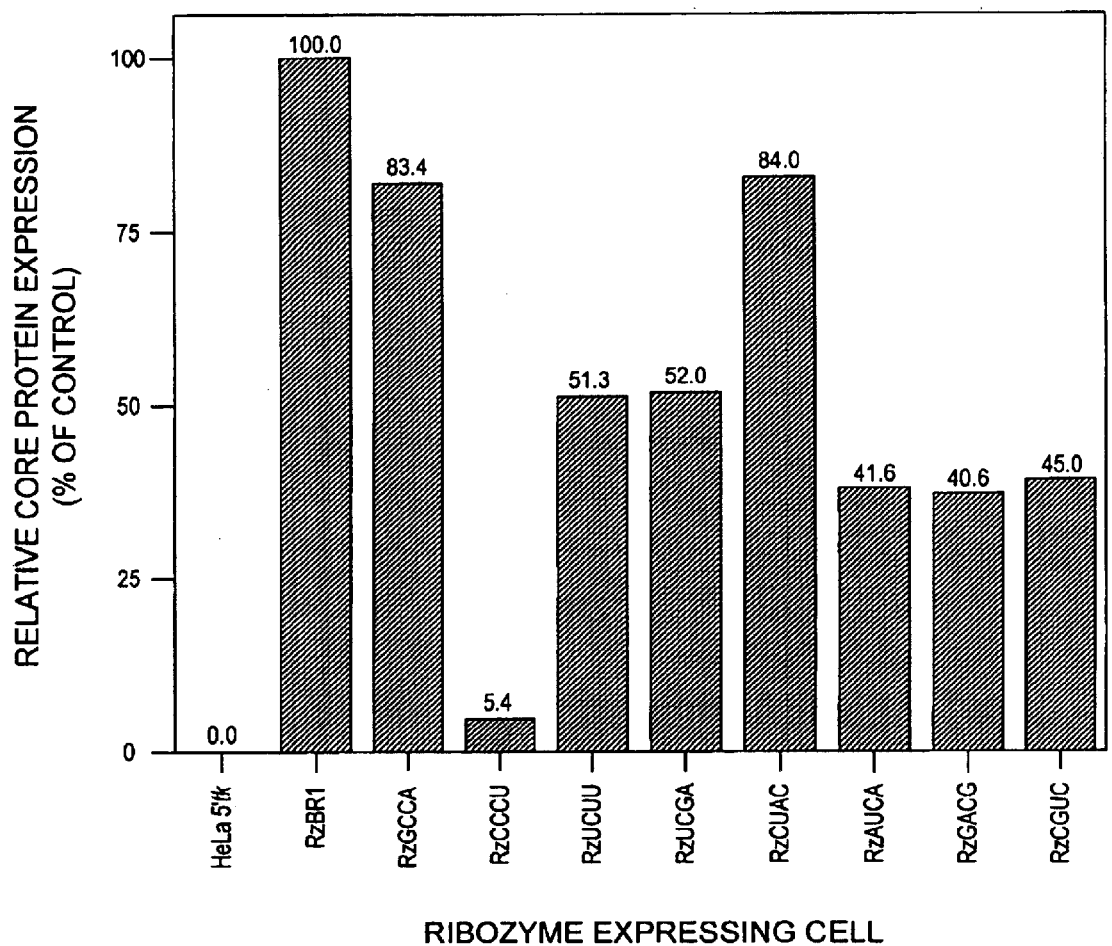

A decrease in Core protein was observed in several candidates (range 16 to 59%, FIG. 8A), with RzHCV8 showing an exceptional decrease in Core protein expression with 95% reduction compared to control Rz transduced cells after GCV selection (FIG. 8B). A reduction in core protein expression to 52% and 42% was observed in GCV-resistant cells derived from RzHCV6 and RzHCV4 transduced cells, respectively, compared to control RzBR1 transduced cells (FIGS. 8A and B). FIG. 8A is a western blot where lane 1 shows protein levels for the HeLa 5'tk parental cells and lanes 2–10 shows the protein levels of cells transduced with respectively BR1, HCV control ribozyme, and HCVB, HCV2, HCV6, HCV5, HCV4, HCV9, and HCV1. FIG. 8B shows the quantitation of the western blot in FIG. 8A. Target validation ribozymes 2 and 4 showed 26% and 35% reduction, respectively. (FIG. 6B) Target validation ribozymes 6–9 showed approximately 70% reduction in core protein (FIG. 7B).

To assure that the observed reductions in Core protein were not caused by reduced levels of RNA transcript, Northern blotting analysis was performed on polyA-RNA extracted from stable Rz expressors after GCV selection. Total RNA (15 µg per lane) extracted from cultures at 80% confluency was separated by formaldehyde/1% agarose gel electrophoresis and transferred to nylon membrane. The RNAs were probed for different parts of the two vector derived transcripts expressed in these cells: probes were directed against the tk part of the bicistronic transcript or against the Core portion of the retroviral vector transcript respectively. $-^{32}P$ dCTP labelled probes were hybridized to the membrane in Quickhyb solution (Stratagene) at 65° C. After washing in 2×SSC/0.1%SDS and exposure to film, quantitation of signal was achieved by phosphimager analysis and computer-assisted denistometry as for the Western procedure. Levels of LTR-Core (4.8 kb) and HSV-tk (2.8 kb) transcripts were normalized to signals derived from GAPDH and expressed as percentage of the signal obtained from control Rz transduced 5'tk cells.

Whereas for RzHCV8 a 20% reduction of Core transcript was detected, all other candidates tested showed a relative Core RNA level of equal or higher compared with control Rz transduced cells. No difference was detected for the expression of GAPDH or tk transcript between the GCV resistant cells derived from single Rz transduction. Comparable levels of tk-transcript between parental cells, 5'-tk and ribozyme expressing cells do not explain the gain of resistance to GCV observed in the ribozyme expressing colonies. All preparations of ribozyme vectors had comparable titer. However, to eliminate differences in expression of the retroviral transcript (harboring the 5' UTR Core transcript) between different Rz vector transduced cells, we used the ratio between expressed Core protein and RNA transcript levels as an indicator of HCV IRES translational activity.

Figure 9:
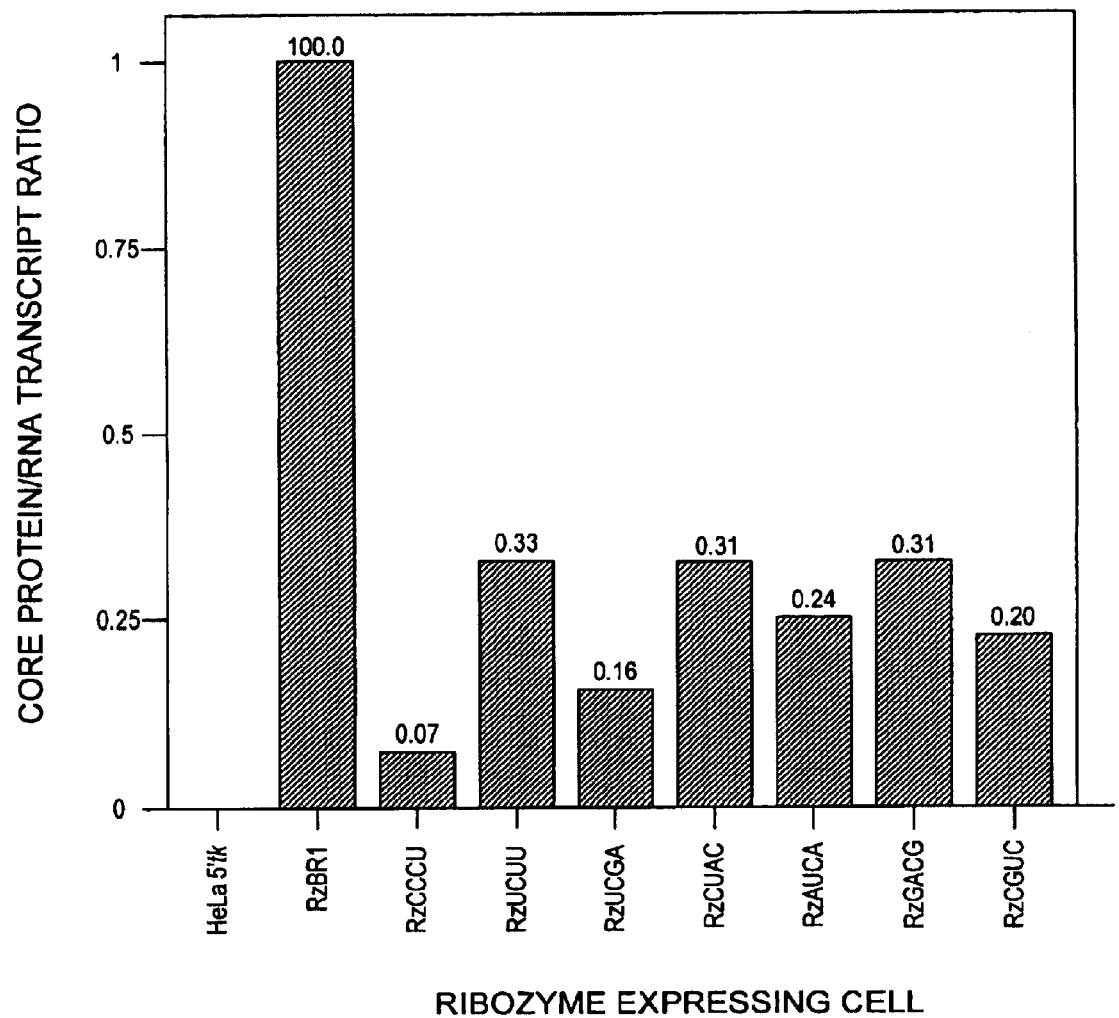
FIG. 9 shows the ratio of core protein to RNA transcripts in ribozyme expressing cells.

The ratio of core protein/RNA transcript in GCV resistant colonies indicates a decrease in IRES activity for several single ribozymes compared with control Rz BR1 transduced, GCV selected cells. The quantitation of these protein levels are shown in FIG. 9. A reduction of HCV IRES-dependent translatability of 83% and 76% was observed for HCV6 and HCV4, respectively (FIG. 9). In contrast, we did not observe any changes in cell growth and cap-dependent translation of cellular proteins (GAPDH, b-actin, c-myc) in GCV- and hygromycin-resistant cells derived from transduction with the functional ribozyme vectors or "validation" ribozymes compared with control Rz transduced cells.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of identifying a compound that modulates the activity of a cellular regulator comprising, contacting a sample containing a cellular regulator and a nucleic acid element acted on by the cellular regulator with a test compound under conditions that allow replication or expression of the nucleic acid element or a gene operatively linked to the nucleic acid element, and measuring the amount of replication or expression of the nucleic acid element or gene, an increase or decrease in the amount of replication or expression in the presence of the test compound compared to the absence of the test compound indicates that the compound has cellular regulator modulatory activity wherein said cellular regulator is eIF2Bγ (SEQ ID NOS: 1, 2, 16 or 35) and said nucleic acid element is an internal ribosome entry site (IRES).

2. The method of claim 1, wherein said test compound decreases the amount of replication or expression of said nucleic acid element or gene, thereby exhibiting cellular regulator inhibitory activity.

3. The method of claim 1, wherein said test compound increases the amount of replication or expression of said nucleic acid element or gene, thereby exhibiting cellular regulator enhancing activity.

4. The method of claim 1, wherein said nucleic acid element is a viral IRES.

5. The method of claim 1, wherein said nucleic acid element is hepatitis C virus IRES.

* * * * *